(12) United States Patent
Kawano

(10) Patent No.: US 10,436,632 B2
(45) Date of Patent: Oct. 8, 2019

(54) TERAHERTZ DETECTION SENSOR AND TERAHERTZ IMAGE MEASUREMENT DEVICE

(71) Applicant: TOKYO INSTITUTE OF TECHNOLOGY, Tokyo (JP)

(72) Inventor: Yukio Kawano, Tokyo (JP)

(73) Assignee: TOKYO INSTITUTE OF TECHNOLOGY, Tokyo (JP)

(*) Notice: Subject to any disclaimer, the term of this patent is extended or adjusted under 35 U.S.C. 154(b) by 0 days.

(21) Appl. No.: 16/062,609

(22) PCT Filed: Dec. 14, 2016

(86) PCT No.: PCT/JP2016/087196
§ 371 (c)(1),
(2) Date: Jul. 31, 2018

(87) PCT Pub. No.: WO2017/104697
PCT Pub. Date: Jun. 22, 2017

(65) Prior Publication Data
US 2018/0364094 A1    Dec. 20, 2018

(30) Foreign Application Priority Data

Dec. 15, 2015  (JP) ................ 2015-244218

(51) Int. Cl.
*G01J 1/02*       (2006.01)
*G01Q 60/22*      (2010.01)
*G01N 21/3581*    (2014.01)

(52) U.S. Cl.
CPC ............ *G01J 1/02* (2013.01); *G01N 21/3581* (2013.01); *G01Q 60/22* (2013.01); *G02F 2203/13* (2013.01)

(58) Field of Classification Search
CPC ....... G01J 1/02; G01N 21/3581; G01Q 60/22; G02F 2203/13
See application file for complete search history.

(56) References Cited

U.S. PATENT DOCUMENTS

| 5,936,237 A | 8/1999 | van der Weide |
| 2010/0006892 A1 | 1/2010 | Kawano et al. |

(Continued)

FOREIGN PATENT DOCUMENTS

| JP | 2010-019585 A | 1/2010 |
| JP | 2010-060284 A | 3/2010 |

(Continued)

OTHER PUBLICATIONS

Extended European Search Report issued in corresponding application No. 16875674.0, dated Jul. 2, 2019.

*Primary Examiner* — Marcus H Taningco
(74) *Attorney, Agent, or Firm* — Maschoff Brennan

(57) ABSTRACT

A terahertz image measurement device includes a terahertz detection sensor, a magnetic field generating unit, and a measurement control unit. The sensor detects near-field light of terahertz light emitted from a sample. The magnetic field generating unit has a coil disposed around the sample and the sensor, and wound to surround the optical axis of terahertz light irradiated on the sensor, and applies to the sensor a magnetic field generated by allowing an electric current to flow through the coil. The measurement control unit changes a value of the electric current flowing through the coil, sets a strength of the magnetic field to a magnetic field value for which a detection signal level of the terahertz light detected by the sensor increases prominently, and allows the magnetic field value to conform to a specific frequency of the terahertz light.

11 Claims, 14 Drawing Sheets

(56) References Cited

U.S. PATENT DOCUMENTS

| | | |
|---|---|---|
| 2010/0051812 A1 | 3/2010 | Kawano et al. |
| 2010/0102233 A1* | 4/2010 | Gelmond ........... G01N 21/3581 |
| | | 250/341.1 |
| 2010/0200755 A1 | 8/2010 | Kawano et al. |
| 2012/0235040 A1* | 9/2012 | Ouchi ....................... G01J 3/42 |
| | | 250/338.4 |
| 2013/0320216 A1 | 12/2013 | Aiko et al. |
| 2017/0062644 A1* | 3/2017 | Koizumi ............... H01L 31/167 |

FOREIGN PATENT DOCUMENTS

| | | |
|---|---|---|
| JP | 2010-206176 A | 9/2010 |
| JP | 2015-155847 A | 8/2015 |
| WO | 2012/108306 A1 | 8/2012 |

\* cited by examiner f=2.06THz f=2.25THz

TERAHERTZ DETECTION SENSOR AND TERAHERTZ IMAGE MEASUREMENT DEVICE

TECHNICAL FIELD

The present invention relates to a terahertz detection sensor adapted to detect a weak terahertz light, and a terahertz image measurement device.

BACKGROUND ART

Terahertz light means an electromagnetic wave, in general definition, having a frequency in the range of 0.1 to 10 THz (where 1 THz=$10^{12}$ Hz), i.e., a wavelength in the range of 0.03 mm to 3 mm belonging to submillimeter-wave region to the far-infrared region.

The terahertz light is expected to be applied in a wide range of fields, ranging from basic science fields such as radio astronomy, materials science, and biomolecular spectroscopy, to practical fields such as security, information communication, environment, and medical care. For example, when carrying out active measurement in which terahertz light is irradiated on an object and an image of reflected light from or transmitted light through the object is measured, a substance that has not been visible heretofore becomes visible.

Use of the active measurement makes it possible to carry out an inspection of poisonous substances in an envelope, detection of explosive substances or dangerous substances in a bag or container, an inspection of foreign substances in foods, an inspection of a semiconductor chip, and the like. Moreover, use of the active measurement also enables an inspection of deterioration degree of works of art, medical applications such as cancer tests, monitoring of real-time moisture in a plant, an inspection of defects of the inside of exterior wall tiles of a space shuttle, and the like.

Techniques using this kind of active measurement by terahertz light are disclosed in Patent Literatures 1 to 3.

The technique disclosed in Patent Literature 1 includes using a semiconductor chip in which two-dimensional electron gas (to be described below) is formed at a constant position from the surface of the chip, and irradiating terahertz light on the semiconductor chip while applying a magnetic field to the semiconductor chip. The technique further includes measuring an electric current that flows through carbon nanotubes by the irradiation, thereby detecting the intensity and frequency of the weak terahertz light. Note that "two-dimensional electron gas" means electrons that move in the two-dimensional plane along the junction interface between a semiconductor and an insulator, or the junction interface between heterogeneous semiconductors. That is to say, the state in which electrons serving as carriers are distributed in the planar form is referred to as two-dimensional electron gas. Note that, in the specification, a heterogeneous semiconductor means a semiconductor of a kind different from the others, or a semiconductor of a structure different from the others, using an inversion layer or the like.

The technique disclosed in Patent Literature 2 includes allowing a graphene (to be described below) to adhere to the surface of a semiconductor chip having an oxide layer formed thereon, and irradiating terahertz light on the graphene while applying a magnetic field to the graphene. The technique further includes measuring an electric current that flows through the semiconductor chip by the irradiation, thereby detecting the intensity and frequency of the weak terahertz light. Note that "graphene" is an atomic monolayer of two-dimensional carbon crystal, and is capable of absorbing light in any energy state because the energy band gap is zero, thus being suited to absorption of light such as terahertz light or infrared light that has extremely low energy and passes through most of the semiconductors.

The technique disclosed in Patent Literature 3 includes irradiating terahertz light (with a wavelength of 4 μm to 10 mm) on an object, and detecting scattered light from an electrode which is an example of the object, as a signal by the scattered-light detector, thereby detecting foreign substances which are included on the surface of the electrode or within the electrode, e.g., foreign metals.

CITATION LIST

Patent Literature

Patent Literature 1: Japanese Unexamined Patent Application Publication No. 2010-60284
Patent Literature 2: Japanese Unexamined Patent Application Publication No. 2010-206176
Patent Literature 3: WO 2012/108306

SUMMARY OF THE INVENTION

Technical Problem

Incidentally, the technique using active measurement by terahertz light such as disclosed in Patent Literatures 1 to 3 described above is beneficial, for example, to detect interaction between molecules in a sample. In the case of infrared light, the above technique is limited to detection of interaction between specific molecules, but in the case of terahertz light, there is no such limitation. Note that the terahertz light has a longer wavelength by three orders than visible light, and the image of molecules by the terahertz light is a coarser image by three orders than the visible light. That is to say, since the molecules each have a nm (nanometer) size, techniques such as described below are required in order to detect and observe an image of molecules by the terahertz light of a mm (millimeter) size.

When a smaller aperture than a wavelength of terahertz light is opened in a metal film and the terahertz light is irradiated on the aperture, most of the terahertz light does not pass through the aperture, but near-field light (evernescent light) leaks to and stays at the opposite side of the aperture. This near-field light is one form of near-field lights that are variously present, and the near-field light is present without having to allow the terahertz light to pass through the aperture.

Moreover, when the near-field light is pierced with a needle made of tungsten, the near-field light is scattered by the needle to be converted into transmitted radiation because the near-field light is confined in a smaller region than a half-wave length of the terahertz light. Detecting the transmitted radiation makes it possible to observe an image of molecules.

However, when the near-field light is pierced with a needle, information the near-field light has is destructed, thus making it impossible to detect an accurate image. Moreover, when a sample associated with biotechnology is used in active measurement, the sample is influenced by irradiation of terahertz light from the outside, depending on the property of the sample. Thus, the active measurement allowing the terahertz light to be irradiated from the outside poses a problem that the image of molecules (sample) is influenced at the time of detection thereof.

For this reason, the image of molecules needs to be measured by passive measurement that allows terahertz light spontaneously emitted from the sample to be measured. However, no technique of carrying out passive measurement of terahertz light is found at this time.

Moreover, even if passive measurement that measures an image of molecules is carried out, the passive measurement has no technique to select an arbitrary terahertz frequency (e.g., 1 THz, 10 THz).

Molecules do not necessarily respond to terahertz light of all frequencies. For example, PHB (energy storage substance within cells) has characteristic resonance frequencies only in the vicinity of 2.4 THz and in the vicinity of 2.9 THz, which are indicated by arrow Y1 and arrow Y2 in FIG. 20. The resonance frequency in the vicinity of 2.4 THz represents an image of hydrogen bond in the PHB molecules, and the resonance frequency in the vicinity of 2.9 THz represents a vibration image of helical conformation in the PHB molecules. The wavelength becomes high only with each resonance frequency, and allowing the operation of detection of terahertz light to conform to each resonance frequency would make it possible to observe images of each resonance frequency of the PHB molecules, but this is impossible at this time.

The present invention has been made in view of the above background, and an object of the present invention is to provide a terahertz detection sensor and a terahertz image measurement device, capable of properly carrying out passive measurement by terahertz light and selecting an arbitrary terahertz frequency in the passive measurement.

Solution to Problem

In order to solve the problems described above, the present invention provides, as one aspect thereof, a terahertz detection sensor adapted to detect terahertz light, the terahertz detection sensor including: a detection point which has a shape of a smaller size than a wavelength of the terahertz light and in which near-field light of the terahertz light is detected; and a semiconductor substrate having the detection point formed on a surface thereof.

Moreover, the present invention provides, as another aspect thereof, a terahertz image measurement device including: the terahertz detection sensor according to the one aspect, adapted to detect near-field light of terahertz light emitted from a sample; a magnetic field generating unit that has a coil disposed around the sample and the terahertz detection sensor, the coil being wound so as to surround an optical axis of the terahertz light irradiated on the terahertz detection sensor from the sample, and applies to the terahertz detection sensor a magnetic field generated by allowing an electric current to flow through the coil; and a measurement control unit that allows an electric current to flow through the coil, changes a value of the flowing electric current to set a strength of the magnetic field to a magnetic field value for which a detection signal level of the terahertz light of the sample detected by the terahertz detection sensor increases prominently, and allows the magnetic field value to conform to a specific frequency of the terahertz light.

Advantageous Effects of the Invention

The present invention allows a terahertz detection sensor and a terahertz image measurement device to be provided, which are capable of properly carrying out passive measurement by terahertz light and selecting an arbitrary terahertz frequency in the passive measurement.

DESCRIPTION OF EMBODIMENTS

Embodiments of the present invention will be hereinafter described with reference to the drawings.

Configuration of Embodiments

Figure 1:
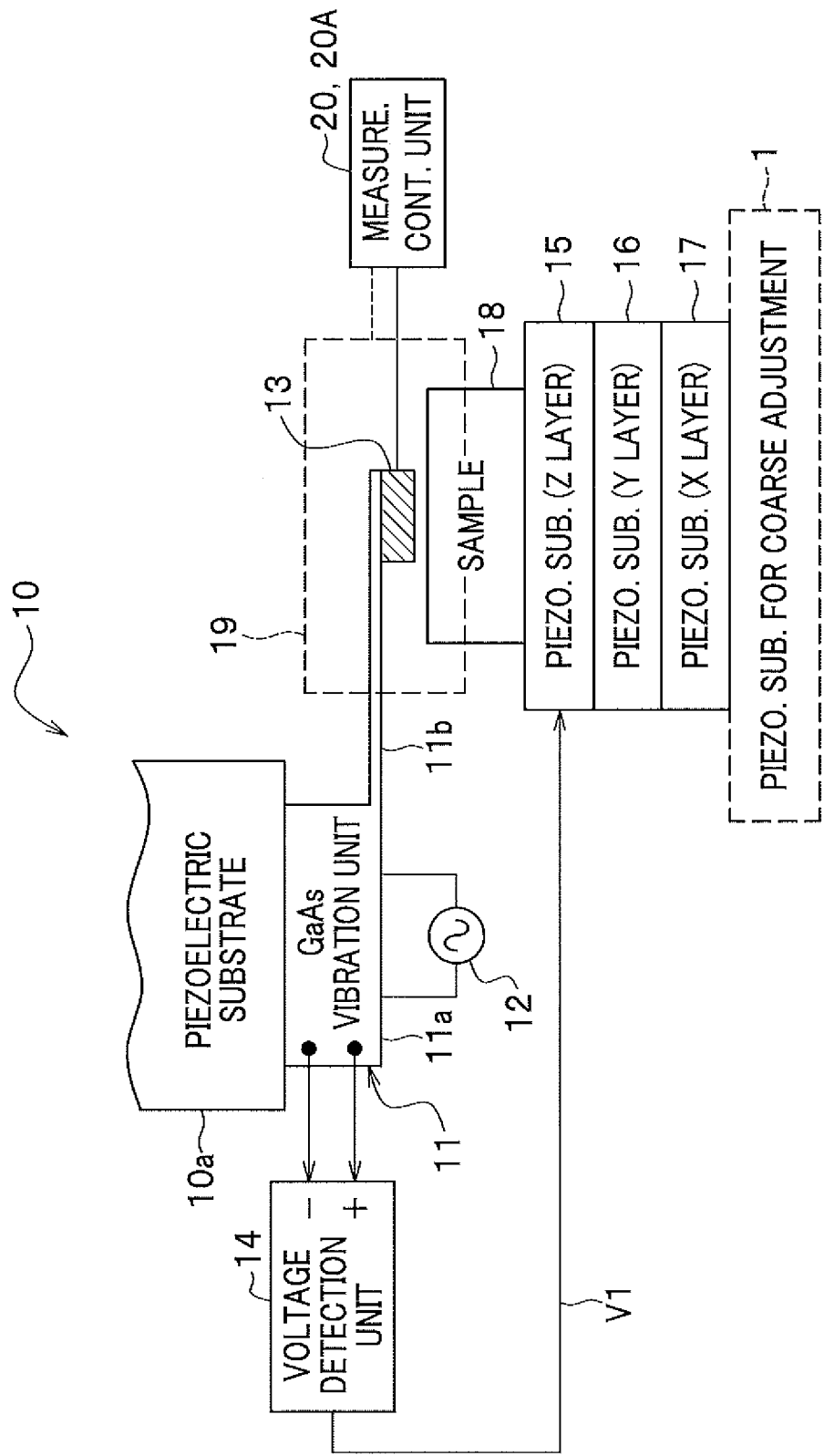
FIG. 1 is a diagram showing a configuration of a terahertz image measurement device using a terahertz detection sensor according to an embodiment of the present invention.

FIG. 1 is a diagram showing a configuration of a terahertz image measurement device using a terahertz detection sensor according to an embodiment of the present invention.

A terahertz image measurement device 10 shown in FIG. 1 is provided with a GaAs (gallium arsenide) vibration unit 11 fixed on a lower end face of a piezoelectric substrate 10a, an AC power supply (power source) 12, a terahertz detection sensor 13, and a voltage detection unit 14. Moreover, the image measurement device 10 is configured to include a piezoelectric substrate for Z layer (Z-piezoelectric substrate) 15, a piezoelectric substrate for Y layer (Y-piezoelectric substrate) 16, a piezoelectric substrate for X layer (X-piezoelectric substrate) 17, a magnetic field generating unit 19, and a measurement control unit 20 composed of a computer or the like. A sample 18 that is an object of terahertz image measurement is mounted and fixed on the Z-piezoelectric substrate 15. Note that the GaAs vibration unit 11 constitutes the vibration unit described in the claims. The vibration unit may be composed of a vibration member formed of piezoelectric material or the like, besides the GaAs vibration unit 11.

The terahertz detection sensor (sensor) 13 is adapted to detect terahertz light spontaneously emitted from the sample 18. Examples of the detection principle include: (1) detecting a terahertz electric field with a gate electrode and modulating an electric current at high speed; (2) using a heating effect because a minute sensor has a low specific heat; (3) using terahertz response of carriers trapped at impurity levels in materials; and (4) using photoconduction associated with electronic excitations of Landau levels in the case of a magnetic field application type sensor to be described below. Note that the above detection principle also applies to a sensor 13A using a graphene 32 shown in FIG. 9 to be described below.

Referring back to FIG. 1, the above detection of terahertz light allows passive measurement by which the measurement control unit 20 measures an image of molecules of the sample 18, to be carried out. The sensor 13 is provided with a terahertz light detection point (detection point) to be described below. The detection point has a planar shape of a smaller size than a wavelength of the terahertz light, allowing the sensor 13 to detect near-field light of the terahertz light at a location near the sample 18. That is, the present embodiment employs the expression "the sensor 13 detects the terahertz light" in some cases, but practically, includes detecting the near-field light of the terahertz light.

The GaAs vibration unit 11 is composed of a base end part 11a having a rectangular parallelepiped shape, and a plate-like part 11b flush with a lower surface of the base end part 11a and projecting from the base end part 11a, which are integrally formed by shaping a GaAs semiconductor material. The sensor 13 is fixed on a lower surface of a tip part of the plate-like part 11b. The detection point is provided on a surface on the opposite side of a fixed surface of the sensor 13. The power source 12 is connected to the base end part 11a, and when a voltage is applied to the base end part 11a from the power source 12, the base end part 11a vibrates with a constant vibration frequency by piezoelectric effect, and in response to this, the plate-like part 11b vibrates vertically with the same vibration frequency.

The voltage detection unit 14 is composed of an inverting amplifier and the like, and detects a voltage that is obtained by detecting an electric current in response to vibration of the GaAs vibration unit 11, and applies a control voltage V1 in response to the detected voltage to the Z-piezoelectric substrate 15. More specifically, the voltage detection unit 14 detects a voltage that is obtained by detecting an electric current in response to vibration of the plate-like part 11b caused by vibration of the base end part 11a, and applies the control voltage V1 in response to the detected voltage to the Z-piezoelectric substrate 15. Note that, where an electric current in response to vibration of the base end part 11a is detected, there are two ways of the case where the electric current is detected from a frequency in the vibration, and the case where the electric current is detected from an amplitude in the vibration.

The Z-piezoelectric substrate 15 is adapted to expand and contract in the Z-direction (vertical direction) in response to magnitude of the control voltage V1, vertically move the sample 18 mounted and fixed on the Z-piezoelectric substrate 15, and keep space between the sample 18 and the sensor 13 at a predetermined interval. This is intended, even where a surface on the sensor 13 side of the sample 18 has an uneven shape, to maintain a detection state of the terahertz light in the sensor 13 at a constant state so as not to allow the detection state to fluctuate.

This will be described in detail. When the Z-piezoelectric substrate 15 causes the sample 18 to gradually come near the sensor 13 to allow the interval between the sample 18 and the sensor 13 to get to a nm (nanometer) order interval, interatomic force acts between the sample 18 and the sensor 13. For example, van der Waals force (attractive force caused by electrostatic interaction acting between molecules) acts. The van der Waals force causes a fixed part of the sensor 13 of the plate-like part 11b to be slightly pulled downward, thus allowing the vibration frequency of the base end part 11a to be slightly deviated. This deviation is detected by the voltage detection unit 14 to be reflected on the control voltage V1. Because of this, the control voltage V1 is fed back to the Z-piezoelectric substrate 15 in the Z-direction so as to allow the deviation to be kept constant, and even where the surface on the sensor 13 side of the sample 18 has an uneven shape, the plate-like part 11b moves vertically so as to allow a distance between the uneven portion and the sensor 13 to be kept constant.

Note that a configuration may be adopted such that the voltage detection unit 14 applies the control voltage V1 to the piezoelectric substrate 10a to cause the piezoelectric substrate 10a to expand and contract in the vertical direction in the same manner as in the Z-piezoelectric substrate 15, thereby keeping the space between the sensor 13 and the sample 18 at the predetermined interval. In this configuration, where the piezoelectric substrate 10a is downsized, a response speed in response to the control voltage V1 becomes high, thus making it possible to vertically move the sensor 13 at high speed relative to the sample 18.

Additionally, the Y-piezoelectric substrate 16 is adapted to expand and contract in the Y-direction (right-left direction) in response to voltage application from an AC power supply (not shown), and the X-piezoelectric substrate 17 is adapted to expand and contract in the X-direction (front-back direction) in response to voltage application. In response to the expansion and contraction, the sample 18 is moved in the right-left and front-back directions, thus making it possible for the sensor 13 to detect terahertz light at a predetermined position on the sample 18. Before performing alignment of the sample 18 using each piezoelectric substrate 15, 16, 17 in this way, it is preferable that a piezoelectric substrate for coarse adjustment is disposed under the X-piezoelectric substrate 17 and a voltage is applied from an AC power supply (not shown) to the piezoelectric substrate 1 for coarse adjustment to coarsely perform alignment of the sample 18.

Figure 2:
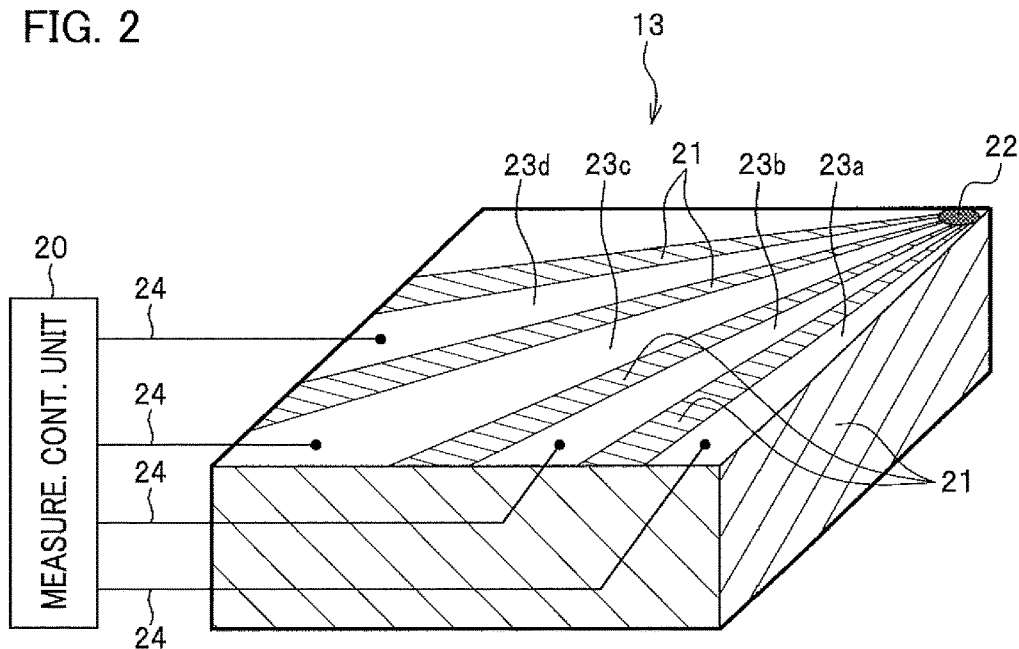
FIG. 2 is a perspective view showing a configuration of the terahertz detection sensor.

FIG. 2 is a perspective view showing a configuration of the terahertz detection sensor 13. The terahertz detection sensor 13 shown in FIG. 2 is configured to include a GaAs substrate 21 having a rectangular parallelepiped shape, a two-dimensional electron gas section (gas section) 22 serving as a terahertz light detection point formed at one corner on an upper surface of the substrate 21, and four electrodes 23a, 23b, 23c, 23d each electrically connected to the gas section 22 and extending separately while widening. Each electrode 23a~23d is formed of conductive material such as gold or the like, and formed so as to allow a connection end thereof to the gas section 22 to be pointed like a needle, and to extend from the needle-like connection end to an edge of the substrate 21 in an elongated fashion while widening in a fan shape. Forming each electrode 23a~23d into a needle shape makes it easy to receive a terahertz wave with an antenna effect.

More specifically, each electrode 23a~23d is formed into a band-like shape extending with a point thereof tapered like a needle, and includes a pair of electrodes joined to the detection point (gas section 22) in the needle-like point. The electrodes have a length equal to or longer than a wavelength (including a half-wave length and a quarter-wave length) of terahertz wave and are adapted to receive the terahertz wave in a region on which an electric field is concentrated, shorter than the wavelength (including the half-wave length and the quarter-wave length) of the terahertz wave.

Conductive wires 24 connected to the measurement control unit 20 are each connected to each of the electrodes 23a~23d. Note that a configuration may be adopted such that two or more conductive wires 24 are connected to one electrode 23a (23b, 23c, 23d) and, even if one of them is disconnected due to breaking of wire, the other wires allow signals to be transmitted.

The measurement control unit 20 is adapted to supply an electric current to the gas section 22 through the conductive wires 24 and two electrodes (e.g., the electrodes 23a, 23d provided on both sides), thereby moving electrons in two-dimensional electron gas of the gas section 22 and allowing the sensor 13 to detect near-field light of the terahertz light emitted from the sample 18. Moreover, the measurement control unit 20 is adapted to receive a detection voltage for the terahertz light detected in the gas section 22, through the conductive wires 24 connected to the other two electrodes 23b, 23c, and to measure a terahertz image of molecules of the sample 18. Note that the two electrodes 23a, 23d through which the electric current is supplied constitute the first electrode described in the claims, and the other two electrodes 23b, 23c through which the detection voltage for the terahertz light is transmitted constitute the second electrode described in the claims.

The sensor 13 is composed of a HEMT (High Electron Mobility Transistor) or the like including two-dimensional electron gas formed at a constant position (distance) from a surface thereof. The HEMT is a transistor using two-dimensional electron gas in which the two-dimensional electron gas is formed by means of modulation doping, and characterized by a high electron-mobility. Accordingly, the sensor 13 is capable of controlling an electron current that flows from a source (not shown) to a drain (not shown) on the two-dimensional electron gas, at high speed using the high electron-mobility, with a gate voltage obtained by detecting the near-field light of the terahertz light emitted from the sample 18. Note that the gate voltage is supplied to a gate (not shown), and the gate, the source and the drain on the two-dimensional electron gas correspond to a gate of a MOSFET (Metal-Oxide-Semiconductor Field-Effect Transistor), the source and the drain on the two-dimensional electron gas.

Figure 3A:
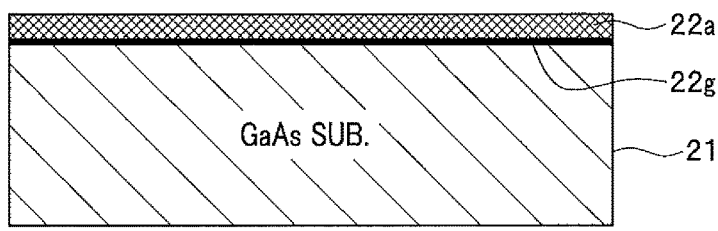
FIG. 3A shows a method of fabrication of the terahertz detection sensor, and is a side view showing a semiconductor substrate having an AlGaAs layer laminated on a GaAs substrate.

In the present embodiment, as shown in FIG. 3A, the sensor 13 is formed using a semiconductor substrate having an AlGaAs (aluminum gallium arsenide) layer 22a laminated on the GaAs substrate 21. In the structure of the semiconductor substrate, two-dimensional electron gas 22g in which electrons moving in the two-dimensional plane are distributed is formed along a junction interface between the GaAs substrate 21 and the AlGaAs layer 22a.

As an alternative semiconductor substrate, a combination of a Si layer and a SiGe (silicon germanium) layer, of an AlGaAs layer and an InGaAs (indium gallium arsenide) layer, or of a GaN (gallium nitride) layer and an AlGaN (aluminum gallium nitride) layer, may be employed.

Figure 3B:
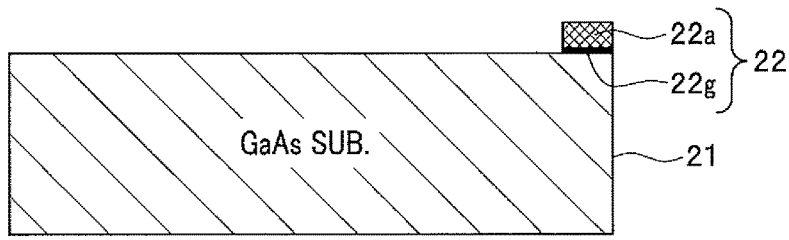
FIG. 3B shows the method of fabrication of the terahertz detection sensor, and is a side view showing a state in which the AlGaAs layer is cut by etching.
Figure 3C:
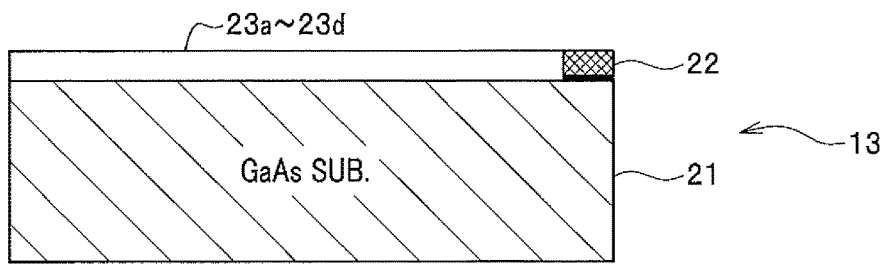
FIG. 3C shows the method of fabrication of the terahertz detection sensor, and is a side view showing a state in which each electrode is formed on the GaAs substrate.

Next, as shown in FIG. 3B, the AlGaAs layer 22a of a rectangular shape in planar view is cut by etching and shaped so as to allow one corner of the rectangular parallelepiped to be left with a smaller size than a wavelength of terahertz light emitted from the sample 18. This shaping allows the two-dimensional electron gas section 22 to be formed by both of the AlGaAs layer 22a left and the two-dimensional electron gas 22g lying on the undersurface side of the AlGaAs layer 22a. Next, as shown in FIG. 3C, conductive material such as gold or the like is vapor-deposited on the GaAs substrate 21 to form each electrode 23a~23d (see FIG. 2), thereby fabricating the sensor 13. Subsequently, each electrode 23a~23d is connected via the conductive wire 24 to the measurement control unit 20 as shown in FIG. 2.

Note that the two-dimensional electron gas section 22 shown in FIG. 3B is formed by etching into a planar shape capable of efficiently detecting near-field light of the terahertz light emitted from the sample 18, for example, into an elliptical shape with a size of 0.8 µm to 1 µm. The planar shape of the gas section 22 may be formed into various shapes such as a circular shape, a polygon, a star shape or the like, as long as the near-field light of the terahertz light can be efficiently detected.

Moreover, the size of the two-dimensional electron gas section 22 is approximately 0.3 µm in the minimum real size under existing circumstances (it is obvious that this size will be further reduced from now on), and other real sizes include approximately 0.9 µm, approximately 2 µm, and approximately 5 µm. These sizes of the gas section 22 correspond to diameter sizes of an aperture provided in a conventional terahertz light detection element (conventional sensor) using active measurement. Note that approximately 0.9 µm, approximately 2 µm, and approximately 5 µm are hereinafter expressed as 0.9 µm, 2 µm, and 5 µm.

The conventional sensor includes an aperture through which part of the terahertz light passes, and which is opened in a metal film provided via a probe on hetero-junction semiconductors including two-dimensional electron gas. The aperture has a smaller diameter size than a wavelength of terahertz light, and when the terahertz light is irradiated from above the metal film toward the aperture, the near-field light leaks to a position of the probe on the opposite side of the aperture, thus allowing the near-field light to be detected via the probe in the two-dimensional electron gas. In contrast, the detection point such as the gas section 22 in the present embodiment makes it possible to detect the near-field light of the terahertz light emitted from the sample 18, by allowing the detection point to come near the sample 18, without having to allow the terahertz light to pass through the aperture.

Figure 4:
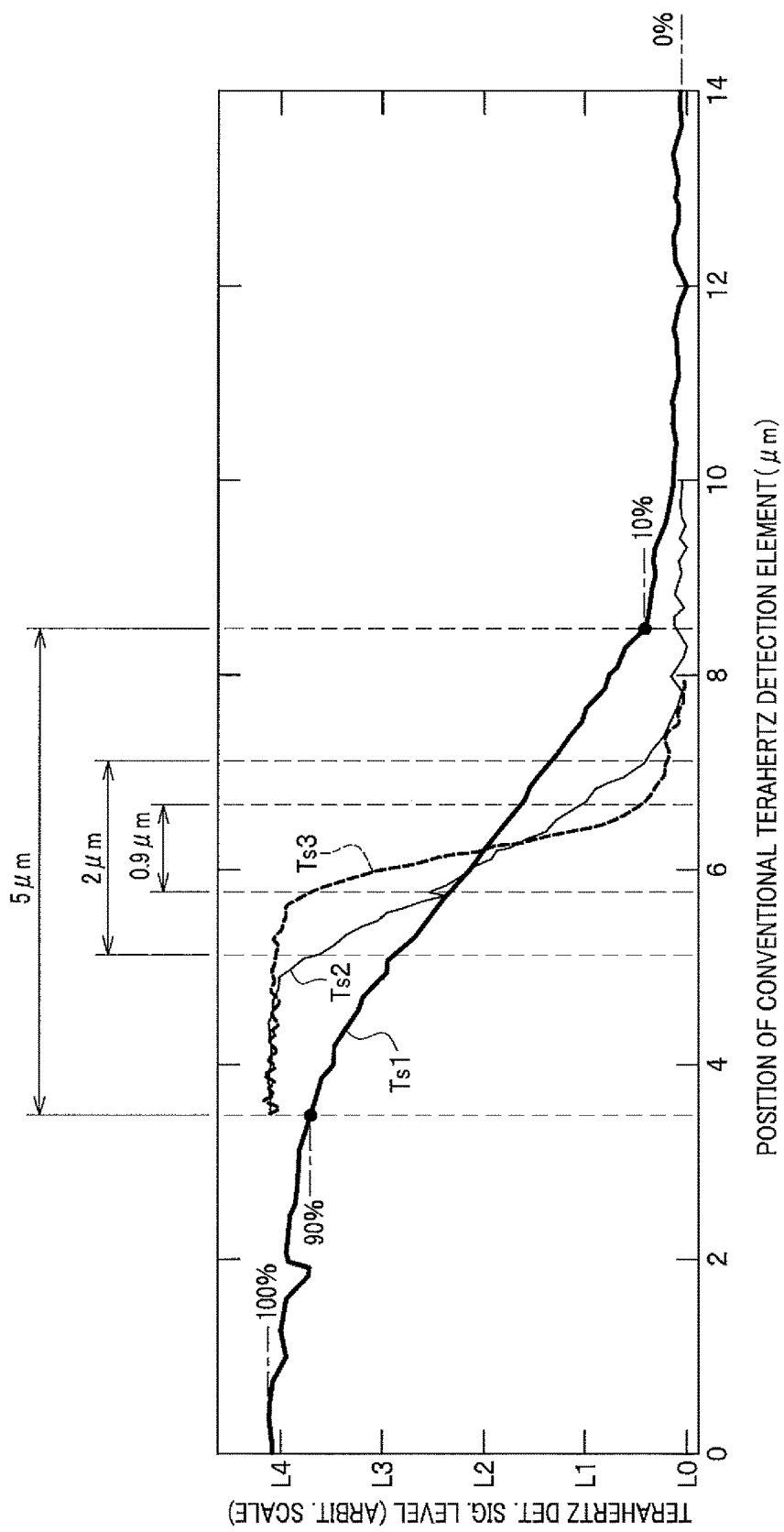
FIG. 4 is a diagram showing a relationship between a position (0~14 μm) of the above conventional terahertz detection element represented in the horizontal axis and a terahertz detection signal level (arbitrary scale: L0~L4) represented in the vertical axis.

FIG. 4 shows a relationship between a position (0~14 µm) of the above conventional terahertz detection element (conventional sensor), which is represented in the horizontal axis, and a terahertz detection signal level (indicated by arbitrary scale L0~L4) based on detection of the near-field light having passed through the aperture, which is represented in the vertical axis. In the position of the terahertz detection element represented in the horizontal axis, the range of 5 µm indicated by a two-way arrow indicates the position of an aperture having the diameter size=5 µm in the conventional sensor. Similarly, the range of 2 µm indicated by a two-way arrow indicates the position of an aperture having the diameter size=2 µm, and the range of 0.9 µm indicated by a two-way arrow indicates the position of an aperture having the diameter size=0.9 µm.

Herein, comparison is made with respect to resolution for the detection of terahertz light in the diameter sizes 0.9 µm, 2 µm, and 5 µm of each aperture shown in FIG. 4.

In the case of the diameter of the aperture being 5 µm, the amount of near-field light of the terahertz light having passed through the aperture is larger than that in the cases of the other apertures (0.9 µm, 2 µm), and accordingly, a falling edge of a terahertz detection signal Ts1 detected by detection of the near-field light becomes gentler than that in the cases of the other apertures (0.9 µm, 2 µm). In this case, the range of 90% to 10% of the maximum value (100%) of the terahertz detection signal Ts1 (or Ts2, Ts3 to be described below) defines resolution. This resolution is determined depending on the size of the aperture (in this case, 5 µm). Therefore, in the case of the diameter of the aperture being 5 µm, the resolution becomes lower than that in the cases of the other apertures (0.9 µm, 2 µm).

In the case of the diameter of the aperture being 2 µm, the amount of near-field light is smaller than that in the case of the diameter of the aperture being 5 µm, and is larger than that in the case of the diameter of the aperture being 0.9 µm, and accordingly, a falling edge of a terahertz detection signal Ts2 becomes steeper than that in the case of the aperture having the diameter of 5 μm. Therefore, in the case of the diameter of the aperture being 2 μm, the resolution becomes higher than that in the case of the aperture having the diameter of 5 μm.

In the case of the diameter of the aperture being 0.9 μm, the amount of near-field light is smaller than that in the case of the diameter of the aperture being 2 μm, and accordingly, a falling edge of a terahertz detection signal Ts3 becomes steeper than that in the case of the aperture having the diameter of 2 μm. Therefore, in the case of the diameter of the aperture being 0.9 μm, the resolution becomes higher than that in the case of the aperture having the diameter of 2 μm.

Even where the size of the two-dimensional electron gas section 22 is set to be 0.9 μm, 2 μm, and 5 μm as in the present embodiment, the same resolution for the detection of terahertz light can be obtained as in the cases of the diameter size of the aperture in the conventional sensor being 0.9 μm, 2 μm, and 5 μm.

Figure 5A:
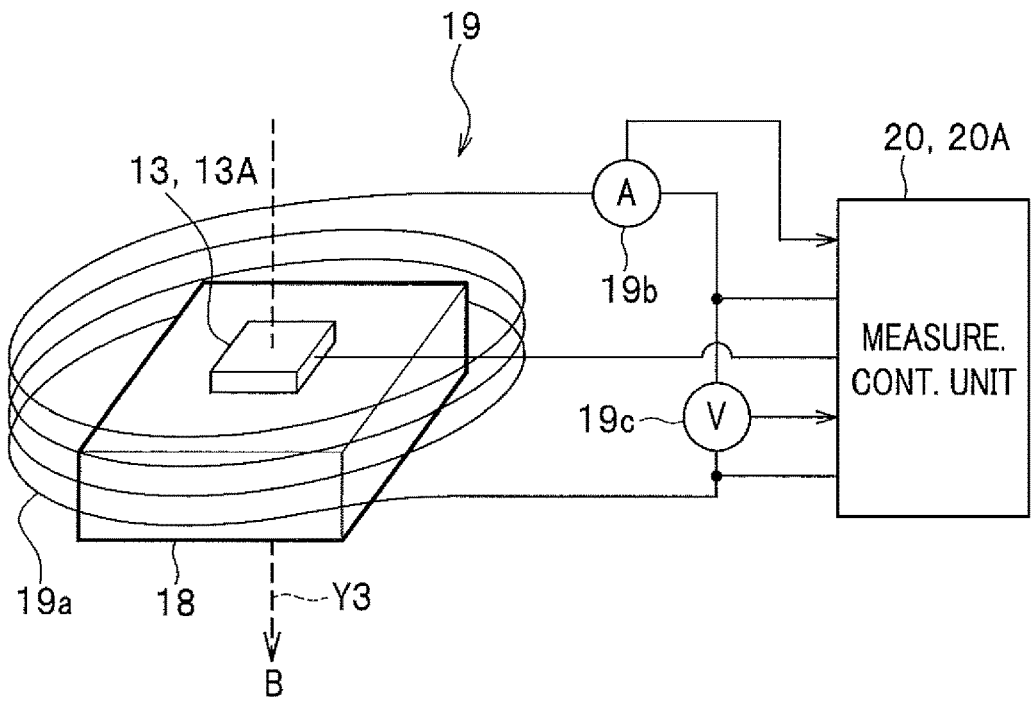
FIG. 5A is a diagram showing a configuration of a magnetic field generating unit.
Figure 5B:
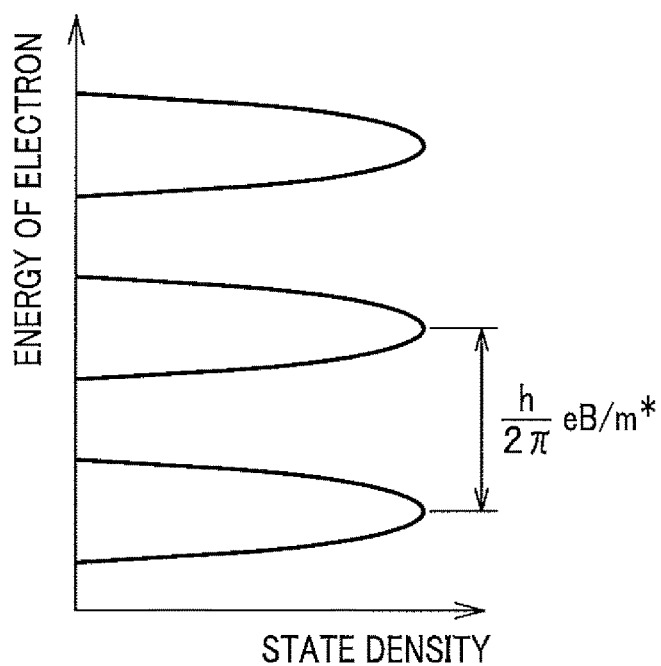
FIG. 5B is a diagram showing formation of Landau levels caused by application of a magnetic field, for explaining the principle of detection of terahertz light.

Next, description will be given of the magnetic field generating unit 19 shown in FIG. 1. FIG. 5A shows a configuration of the magnetic field generating unit 19, and FIG. 5B shows formation of Landau levels caused by application of a magnetic field, for explaining the principle of detection of terahertz light. The Landau levels mean discontinuous (discrete) energy levels which are obtainable when charged particles make cyclotron motion (circular motion) in a magnetic field.

As shown in FIG. 5A, the magnetic field generating unit 19 is configured to include a coil 19a wound so as to surround an optical axis of terahertz light that is emitted from the sample 18 to be irradiated on the sensor 13, an ammeter 19b adapted to detect an electric current (coil current) that flows through the coil 19a, and a voltmeter 19c adapted to detect a voltage across both ends of the coil 19a. The magnetic field generating unit 19 allows an electric current to flow through the coil 19a, thereby generating a magnetic field B indicated by a dashed line arrow Y3 to apply it to the sensor 13. The magnetic field B can be uniquely determined from the coil current.

In FIG. 5B, the horizontal axis indicates a state density and the vertical axis indicates energy of electron. As shown in FIG. 5B, when photon energy hf of terahertz light emitted from the sample 18 is equal to energy spacing in Landau levels represented by the following formula (1), very large absorption of the terahertz light is caused.

$$(h/2\pi)e\ B/m^* \quad (1)$$

This phenomenon is called cyclotron absorption, or cyclotron resonance.

Herein, h denotes Planck constant; e denotes elementary charge; B denotes a magnetic field; and m* denotes effective mass of electrons in crystal (for example, in the case of GaAs, the effective mass is approximately 0.0665 times larger than the mass of free electrons).

The photon energy hf of terahertz light obtained when cyclotron absorption is caused becomes equal to the energy spacing in Landau levels obtained when cyclotron absorption is caused. That is, the following formula (2) is established.

$$hf = (h/2\pi)eB/m^* \quad (2)$$

Based on the formula (2), the frequency f of terahertz light can be determined from the magnetic field B obtained when cyclotron absorption is caused, because h, e, and m* other than the magnetic field B are known constants.

The terahertz image measurement device 10 (FIG. 1) according to the present embodiment uses cyclotron absorption in the two-dimensional electron gas section 22. The measurement control unit 20 of the device 10 changes the strength (magnetic field value) of the magnetic field B applied to the sensor 13 while changing the value of an electric current which flows through the coil 19a, and allows the magnetic field value to be set to a magnetic field value for which the terahertz detection signal level of the sample 18 detected by the sensor 13 increases prominently. The frequency of the terahertz detection signal with the prominently increased level defines a characteristic resonance frequency (specific frequency). Therefore, the magnetic field value can be allowed to conform to the specific frequency by allowing the magnetic field value to be set to the position at which the detection signal level increases prominently. In other words, the terahertz frequency can be selected. Note that, when the measurement control unit 20 allows the magnetic field value to conform to the specific frequency, it reads from the ammeter 19b the value of an electric current which flows through the coil 19a, and reads from the voltmeter 19c the level of the terahertz detection signal.

The above frequency of the terahertz detection signal with the prominently increased level defines a characteristic resonance frequency (specific frequency). For example, the magnetic field B to be generated by the magnetic field generating unit 19 under control of the measurement control unit 20 may be set as shown in FIG. 6A to FIG. 6E. The example of FIG. 6A allows the specific frequency f=0.7 THz to be selected for a magnetic field value of approximately 2 [T] for which the signal level steeply increases to 1, thereby making it possible to display a terahertz image of molecules of the sample 18 that emits a terahertz light with the selected frequency.

Figure 6A:
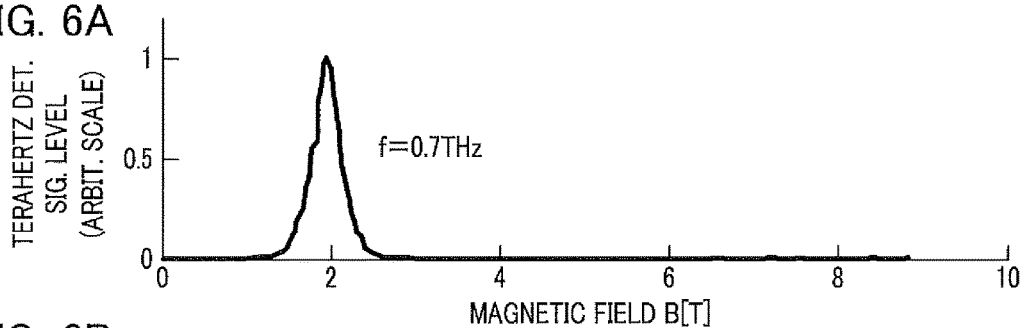
FIG. 6A shows a waveform of terahertz light with a specific frequency f in the case where a terahertz detection signal level in the vertical axis steeply increases for a predetermined magnetic field value in the horizontal axis, and is a diagram showing a waveform of terahertz light with the specific frequency f=0.7 THz.
Figure 6B:
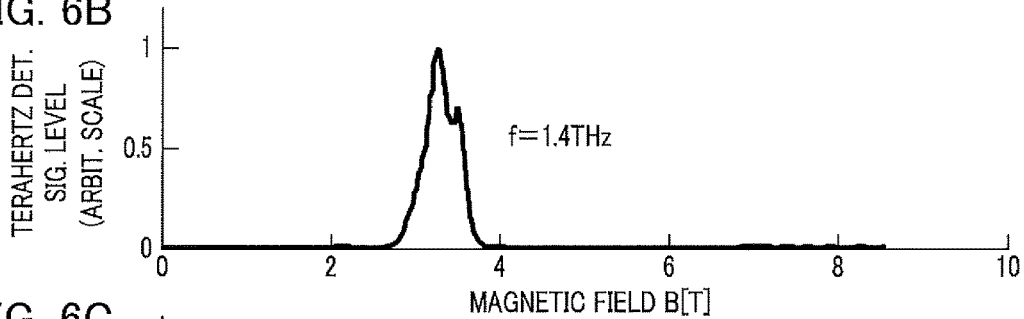
FIG. 6B shows a waveform of terahertz light with a specific frequency f in the case where a terahertz detection signal level in the vertical axis steeply increases for a predetermined magnetic field value in the horizontal axis, and is a diagram showing a waveform of terahertz light with the specific frequency f=1.4 THz.
Figure 6C:
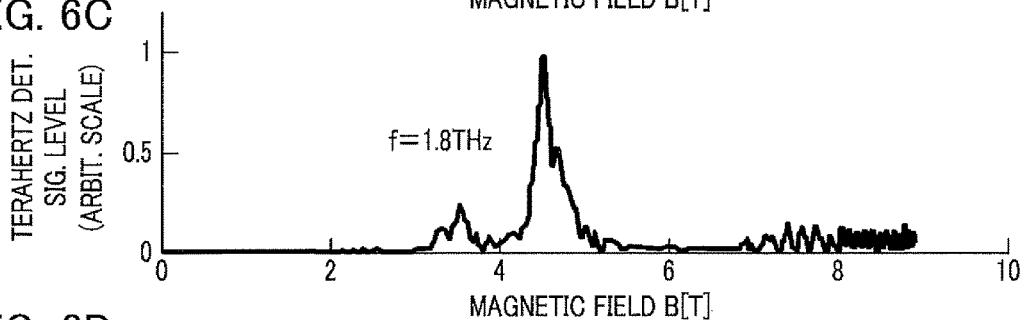
FIG. 6C shows a waveform of terahertz light with a specific frequency f in the case where a terahertz detection signal level in the vertical axis steeply increases for a predetermined magnetic field value in the horizontal axis, and is a diagram showing a waveform of terahertz light with the specific frequency f=1.8 THz.
Figure 6D:
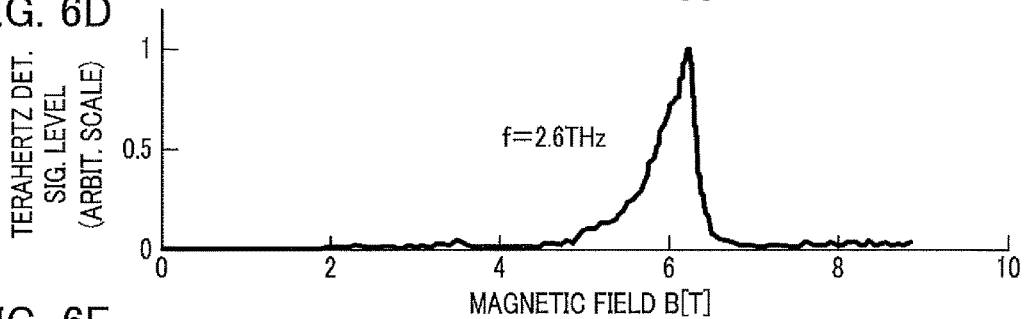
FIG. 6D shows a waveform of terahertz light with a specific frequency f in the case where a terahertz detection signal level in the vertical axis steeply increases for a predetermined magnetic field value in the horizontal axis, and is a diagram showing a waveform of terahertz light with the specific frequency f=2.6 THz.
Figure 6E:
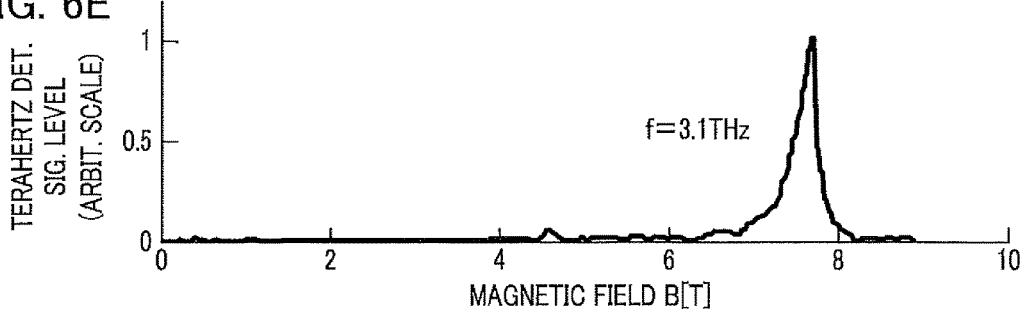
FIG. 6E shows a waveform of terahertz light with a specific frequency f in the case where a terahertz detection signal level in the vertical axis steeply increases for a predetermined magnetic field value in the horizontal axis, and is a diagram showing a waveform of terahertz light with the specific frequency f=3.1 THz.

In a similar way, the example of FIG. 6B allows the specific frequency f=1.4 THz to be selected for a magnetic field value of approximately 3 [T] for which the signal level steeply increases to 1; the example of FIG. 6C allows the specific frequency f=1.8 THz to be selected for a magnetic field value of approximately 4.5 [T] for which the signal level steeply increases to 1; the example of FIG. 6D allows the specific frequency f=2.6 THz to be selected for a magnetic field value of approximately 6 [T] for which the signal level steeply increases to 1; and the example of FIG. 6E allows the specific frequency f=3.1 THz to be selected for a magnetic field value of approximately 7.5 [T] for which the signal level steeply increases to 1, thereby making it possible to display terahertz images of molecules of the sample 18 that emits terahertz lights with the above selected frequencies, respectively.

Figure 7A:
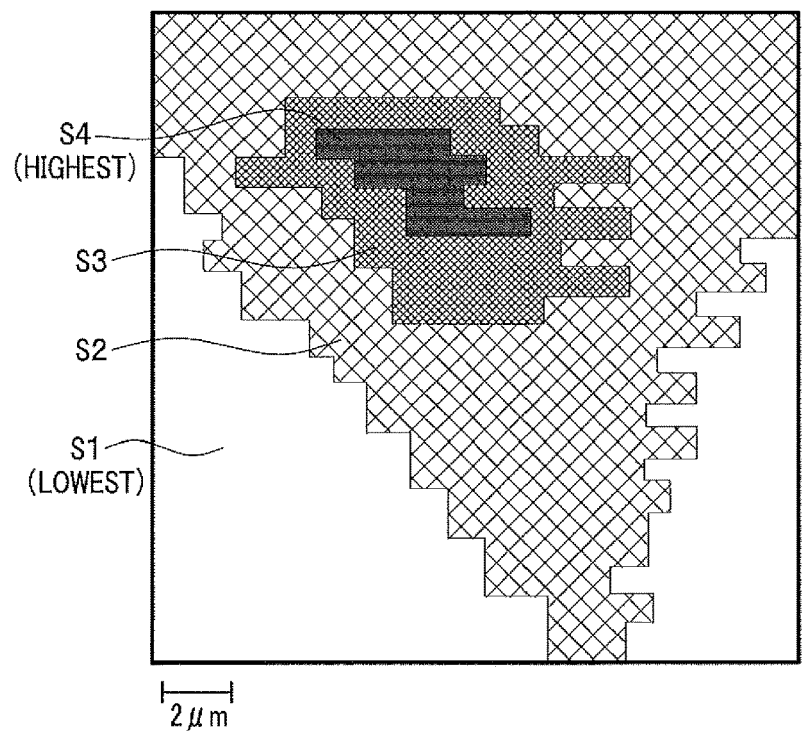
FIG. 7A shows terahertz light emission intensity distribution obtained when changing the magnetic field value to select a frequency of terahertz light and actually measuring the distribution of light emission intensity of the selected terahertz light, and is a diagram showing the light emission intensity distribution in a case of the frequency f=2.06 THz.
Figure 7B:
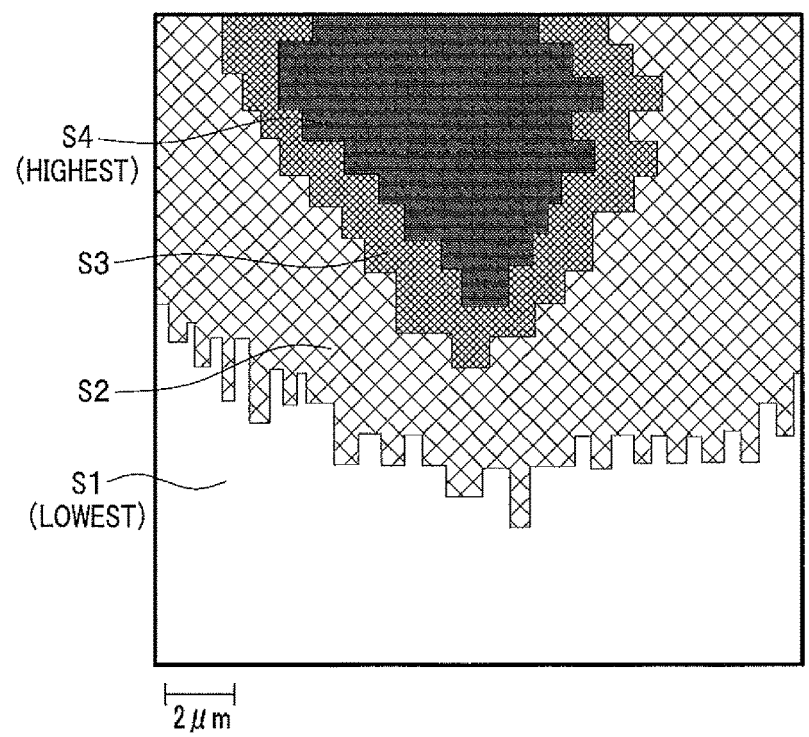
FIG. 7B shows terahertz light emission intensity distribution obtained when changing the magnetic field value to select a frequency of terahertz light and actually measuring the distribution of light emission intensity of the selected terahertz light, and is a diagram showing the light emission intensity distribution in a case of the frequency f=2.25 THz.

FIGS. 7A and 7B are diagrams each showing terahertz light emission intensity distribution obtained when changing the magnetic field value to select a frequency of terahertz light and actually measuring the distribution of light emission intensity of the selected terahertz light, by passive measurement. FIG. 7A is a diagram showing the light emission intensity distribution in a case of the frequency f=2.06 THz, with reference signs S1 (lowest) to S4 (highest) from a low intensity to a high intensity in order. FIG. 7B is a diagram showing the light emission intensity distribution in a case of the frequency f=2.25 THz, with the reference signs S1 (lowest) to S4 (highest). Note that the present experiment was conducted using a vibration member other than the GaAs vibration unit 11 of the terahertz image measurement device 10.

In the case of the frequency f=2.06 THz shown in FIG. 7A, the light emission intensity of terahertz light is low in a lower left corner region and in a lower right corner region as indicated by the reference sign S1, and becomes higher as going upward toward the center from the corner regions as indicated by the reference signs S2, S3 and S4. In the case of the frequency f=2.25 THz shown in FIG. 7B, the light emission intensity of terahertz light is low in the lower region as indicated by the reference sign S1, and becomes higher as going upward from the lower region as indicated by the reference signs S2, S3 and S4.

Figure 8:
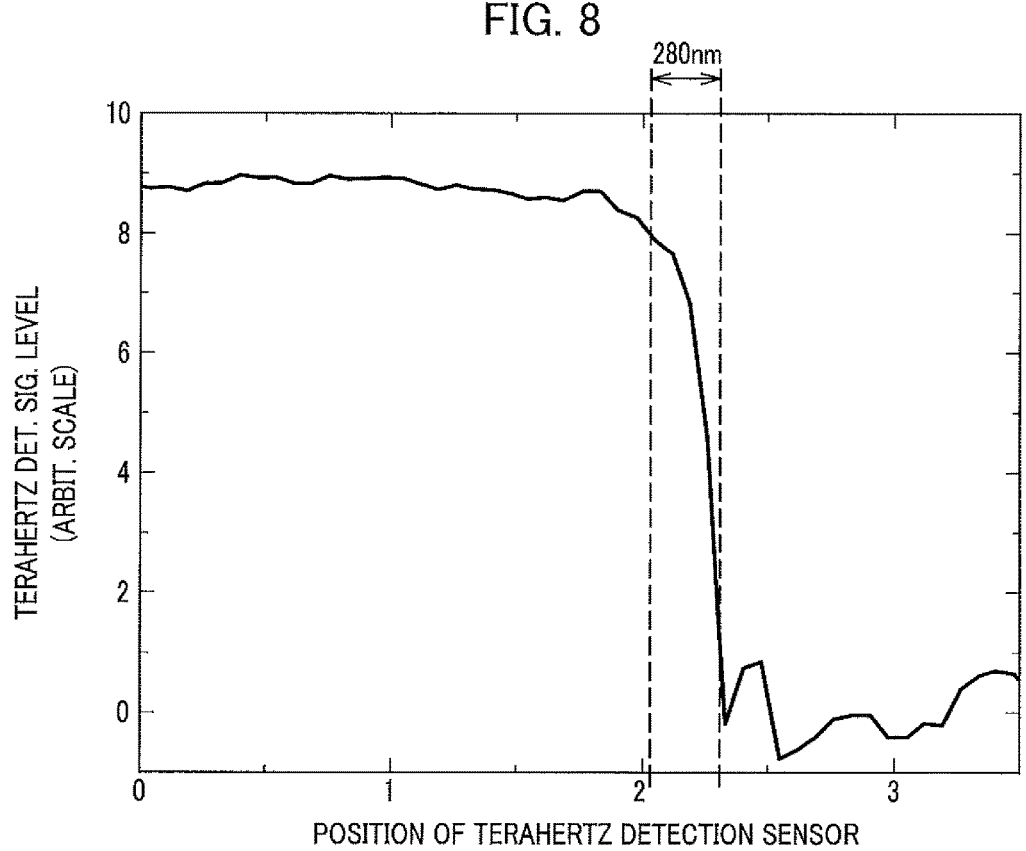
FIG. 8 is a diagram showing a relationship between a position of the sensor represented in the horizontal axis and a terahertz detection signal level obtained by the sensor represented in the vertical axis, the relationship being obtained when conducting an experiment in active measurement by means of the terahertz image measurement device according to the present embodiment.

Moreover, FIG. 8 shows a relationship between a position (0~3.5 μm) of the sensor 13 represented in the horizontal axis and a terahertz detection signal level (arbitrary scale: 0~10) based on detection of the near-field light obtained by the sensor 13, represented in the vertical axis, the relationship being obtained when conducting an experiment in active measurement by means of the terahertz image measurement device 10. Note that the present experiment was conducted using a vibration member other than the GaAs vibration unit 11 of the terahertz image measurement device 10. The position of the sensor 13 lies between approximately 2 μm and approximately 2.3 μm, and spatial resolution defined by the above range of 90% to 10% of the maximum value (100%) of the terahertz detection signal is enhanced to 280 nm. In the high resolution of 280 nm, the near-field light of the terahertz light emitted from the sample 18 was detected. At this time of detection, a falling edge of the terahertz detection signal becomes steep as shown in FIG. 8.

Advantageous Effects of the Embodiment

As described above, the terahertz detection sensor 13 and the terahertz image measurement device 10 according to the present embodiment allow the following advantageous effects to be obtained.

(1) The sensor 13 that detects terahertz light is configured to include a detection point which has a shape of a smaller size than a wavelength of the terahertz light and in which, when the terahertz light is irradiated, near-field light of the terahertz light is detected; and a semiconductor substrate having the detection point formed on the surface thereof.

This configuration makes it possible, when the terahertz light spontaneously emitted from the sample is irradiated on the detection point while supplying an operating current to the detection point, to detect the near-field light of the irradiated terahertz light because the detection point has a shape of a smaller size than a wavelength of the terahertz light. The near-field light has a shorter wavelength than a half-wave length of the terahertz light, thus making it possible to measure an image of molecules of a nm (nanometer) size of the sample at high resolution by setting the size of the detection point to a size corresponding to the shorter wavelength. This measurement is passive measurement by which the terahertz light spontaneously emitted from the sample is measured.

Also, it is possible to eliminate defects such as encountered in the conventional active measurement, i.e., when the near-field light of the terahertz light having passed through the aperture opened in the metal film is pierced with a needle made of tungsten, information the near-field light has is destructed. Consequently, an image of molecules of the sample can be properly measured. Therefore, the passive measurement using the terahertz light can be properly carried out and an arbitrary terahertz frequency can be selected in the passive measurement.

(2) The above sensor includes the configuration such that the first electrode 23a, 23d adapted to supply an electric current to the detection point, and the second electrode 23b, 23c adapted to output a voltage detected at a time of detection of the near-field light, to the detection point to which the electric current is supplied through the first electrode 23a, 23d, are formed on the surface of the semiconductor substrate in the sensor 13.

This configuration makes it possible to supply an operating current to the detection point through the first electrode 23a, 23d. Moreover, when the near-field light of the terahertz light emitted from the sample is detected in the detection point, the detected voltage can be output through the second electrode 23b, 23c to the external measurement control unit. Consequently, the measurement control unit 20 can measure an image of molecules of a nm (nanometer) size of the sample at high resolution.

(3) The above sensor includes the configuration such that each of the first electrode 23a, 23d and the second electrode 23b, 23c is formed into a band-like shape extending with a point thereof tapered like a needle and includes a pair of electrodes joined to the detection point in the needle-like point.

This configuration allows the point of each of the first electrode 23a, 23d and the second electrode 23b, 23c to extend with being tapered like a needle, thus making it possible to enhance receiving sensitivity of the terahertz wave with an antenna effect.

(4) The above sensor includes the configuration such that each of the first electrode 23a, 23d and the second electrode 23b, 23c is formed into a band-like shape extending with a point thereof tapered like a needle and includes a pair of electrodes joined to the detection point in the needle-like point, and the electrodes have a length equal to or longer than a wavelength (including a half-wave length and a quarter-wave length) of terahertz wave and are adapted to receive the terahertz wave in a region on which an electric field is concentrated, shorter than the wavelength (including the half-wave length and the quarter-wave length) of the terahertz wave.

This configuration allows the point of each of the first electrode 23a, 23d and the second electrode 23b, 23c to extend with being tapered like a needle, and allows the pair of electrodes in the extending point to have a length equal to or longer than the wavelength of the terahertz wave and to receive the terahertz wave in the region on which an electric field is concentrated, shorter than the wavelength of the terahertz wave, thus making it possible to further enhance receiving sensitivity of the terahertz wave with an antenna effect.

(5) The above semiconductor substrate has a high electron mobility transistor structure in which the AlGaAs layer 22a is laminated on the GaAs layer 21 and the two-dimensional electron gas 22g is distributed in the interface between the AlGaAs layer 22a and the GaAs layer 21. The above detection point has a structure in which the AlGaAs layer 22a is formed into a shape of a smaller size than a wavelength of the terahertz light and the two-dimensional electron gas 22g is distributed in the interface between the formed AlGaAs layer 22a and the GaAs layer 21.

This configuration makes it possible to detect the near-field light of terahertz light spontaneously emitted from the sample in the two-dimensional electron gas 22g serving as the detection point. The high electron mobility transistor in which the two-dimensional electron gas 22g allowing the detection is formed makes it possible to detect the near-field light at high speed because it has a high electron-mobility.

(6) The terahertz image measurement device 10 is configured as follows. That is, the device includes the above sensor 13 adapted to detect near-field light of terahertz light emitted from the sample 18, and the magnetic field generating unit 19 that has the coil 19a disposed around the sample 18 and the sensor 13, the coil 19a being wound so as to surround the optical axis of the terahertz light irradiated on the sensor 13 from the sample 18, and applies to the sensor 13 a magnetic field generated by allowing an electric current to flow through the coil 19a. Moreover, the device includes the measurement control unit 20 that allows an electric current to flow through the coil 19a, changes a value of the flowing electric current to set a strength of the magnetic field to a magnetic field value for which a detection signal level of the terahertz light of the sample detected by the sensor 13 increases prominently, and allows the magnetic field value to conform to a specific frequency of the terahertz light.

This configuration makes it possible to allow the magnetic field value to conform to the specific frequency by allowing the magnetic field value to be set to the position at which the detection signal level of the terahertz light detected by the sensor 13 increases prominently. In other words, the terahertz frequency can be selected. Consequently, an image of molecules of the sample that emits terahertz light with the selected frequency can be displayed.

(7) The terahertz image measurement device is configured to further include the GaAs vibration unit 11 that causes the sensor 13 fixed on the tip of the plate-like part 11b extending from the base end part 11a, to vibrate in the direction of space between the sensor and the sample 18, by application of a voltage to the base end part 11a; and the Z-piezoelectric substrate 15 that mounts and fixes the sample 18 thereon via the space between the sensor 13 and the sample 18, and moves the sample mounted and fixed thereon in the direction of space so as to keep the space constant, in response to a voltage obtained by detecting vibration of the GaAs vibration unit 11.

According to this configuration, when van der Waals force obtained when the interval between the sample 18 and the sensor 13 gets to a nm order interval causes the tip of the plate-like part 11b extending from the base end part 11a to be slightly pulled to the sample side, the vibration frequency of the GaAs vibration unit 11 is slightly deviated. This deviation is reflected on a voltage obtained by detecting vibration of the vibration unit 11, and the voltage is fed back to the Z-piezoelectric substrate 15 in the direction of movement so as to allow the deviation to be kept constant, and even where the surface on the sensor 13 side of the sample 18 has an uneven shape, the tip of the plate-like part 11b vertically moves so as to allow the distance between the uneven portion and the sensor 13 to be kept constant. Therefore, the detection state of the terahertz light in the sensor 13 can be maintained at a constant state so as not to allow the detection state to fluctuate.

<Another Example of the Terahertz Detection Sensor>

Figure 9:
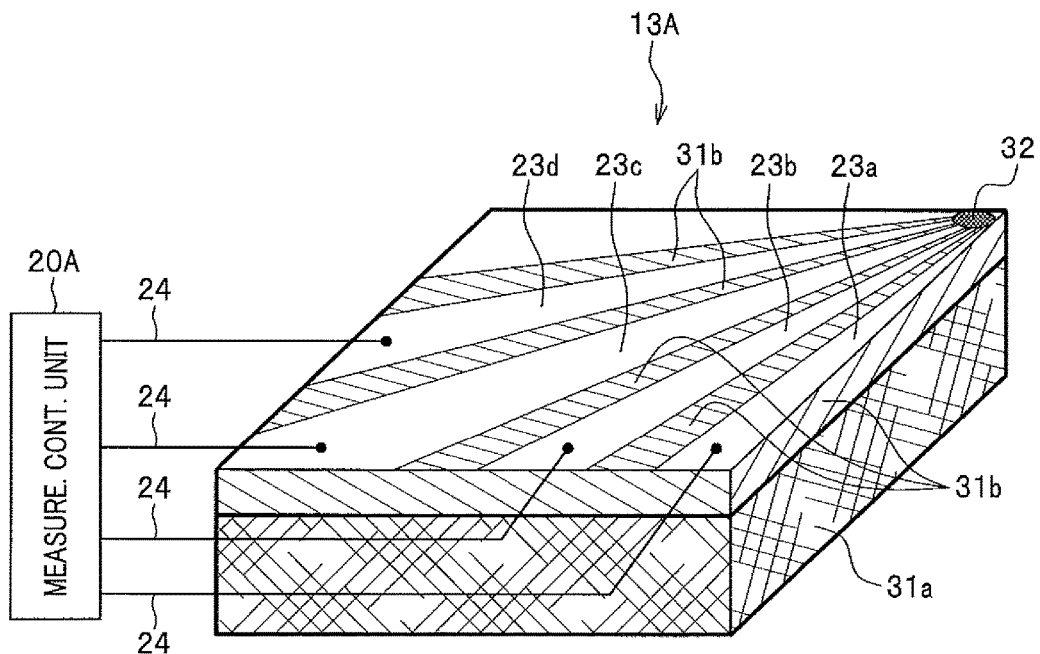
FIG. 9 is a perspective view showing a configuration of a terahertz detection sensor as another example.

FIG. 9 is a perspective view showing a configuration of a terahertz detection sensor 13A as another example. The sensor 13A shown in FIG. 9 is used as the sensor 13 of the terahertz image measurement device 10 shown in FIG. 1.

The sensor 13A shown in FIG. 9 is configured to include a Si (silicon) substrate 31a having a rectangular parallelepiped shape, a $SiO_2$ (silicon dioxide) substrate 31b laminated on the Si substrate 31a, a graphene 32 serving as a terahertz light detection point formed at one corner on an upper surface of the $SiO_2$ substrate 31b, and the same four electrodes 23a~23d as described above, which are electrically connected to the graphene 32. Conductive wires 24 connected to a measurement control unit 20A are each connected to each of the electrodes 23a~23d. Moreover, the sensor 13A is also disposed together with the sample 18 as shown in FIG. 5A described above, so as to be surrounded by the coil 19a of the magnetic field generating unit 19.

The measurement control unit 20A is adapted to allow an electric current to flow through the conductive wires 24 to two electrodes (e.g., the electrodes 23a, 23d provided on both sides), thereby moving electrons in the graphene 32 and allowing the sensor 13A to detect near-field light of the terahertz light emitted from the sample 18. Moreover, the measurement control unit 20A is adapted to receive an output voltage for the near-field light of the terahertz light detected in the graphene 32, from the other two electrodes 23b, 23c through the conductive wires 24, and to measure a terahertz image of molecules of the sample 18.

Figure 10A:
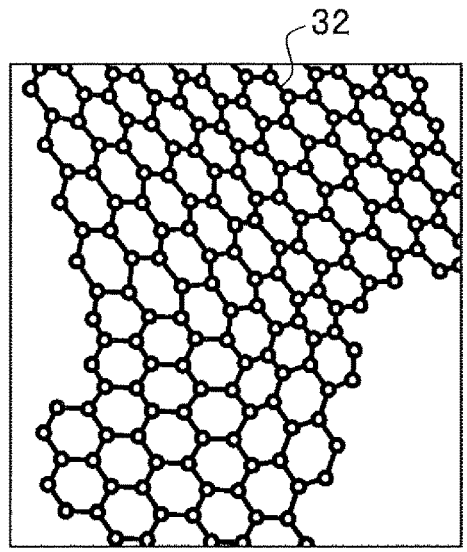
FIG. 10A is a diagram showing a monolayer of honeycomb or hexagonal lattice structure of graphene.

As shown in FIG. 10A, the graphene 32 employs a monolayer of honeycomb or hexagonal lattice structure formed of carbon atoms and each chain between them, and has the form of a sheet of wire netting. Here, in semiconductors such as silicon or other three-dimensional materials, charge carriers each form a quasi-particle because they interact with a periodical field of atomic lattice. However, a quasi-particle in the graphene 32 has characteristics different from characteristics of such three-dimensional materials.

Figure 10B:
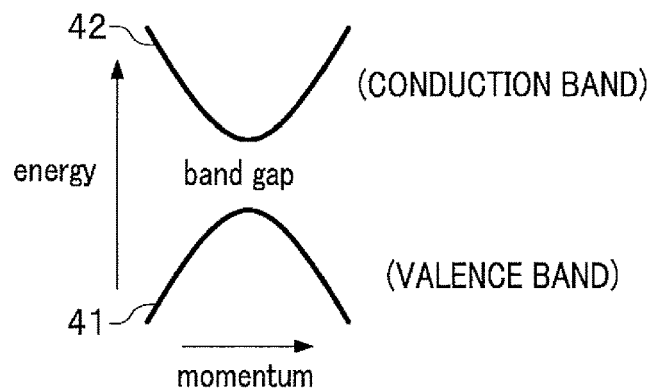
FIG. 10B is a diagram showing an energy band of a typical three-dimensional semiconductor.

As shown in FIG. 10B representing energy in the vertical axis and momentum in the horizontal axis, an energy band of a typical three-dimensional semiconductor includes a valence band located on a lower side and forming the shape of a parabola 41, and a conduction band located on an upper side and forming the shape of a parabola 42 that faces an opposite direction to the parabola 41 in the up-down direction. There is an open band gap between the valence band and the conduction band.

Figure 10C:
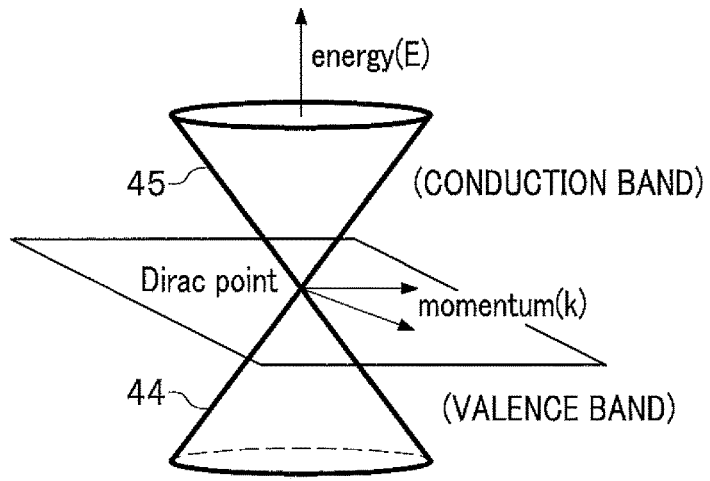
FIG. 10C is a diagram showing an energy band of the graphene.

In contrast, an energy band of the graphene 32 has the form of two cones 44, 45 having apexes come into contact with each other, as shown in FIG. 10C. The point of contact of two cones 44, 45 is called Dirac point. The energy band of this form is characterized by energy E of a quasi-particle behaving like a Dirac-Fermion that is an electron of zero-mass, and momentum k. This quasi-particle moves at a speed of about several percent (%) of the speed of light. From the special band structure like this, it is known that electron mobility in the graphene 32 is extremely high (10 times to 100 times higher than a normal semiconductor) even at room temperature.

Moreover, it is ascertained that Fermi energy (chemical potential in the Fermi particle system at absolute zero) in a normal three-dimensional material such as a semiconductor is proportional to a carrier density, while Fermi energy in the graphene 32 is proportional to the square root of a carrier density. Moreover, the graphene 32 has a symmetrical structure that allows the valence band and the conduction band to coincide with each other at the Dirac point, thus making it possible to make the carrier not only an electron but also a hole (symmetry of the electron and the hole) by applying a gate voltage (by increasing or decreasing the Fermi energy).

Figure 11A:
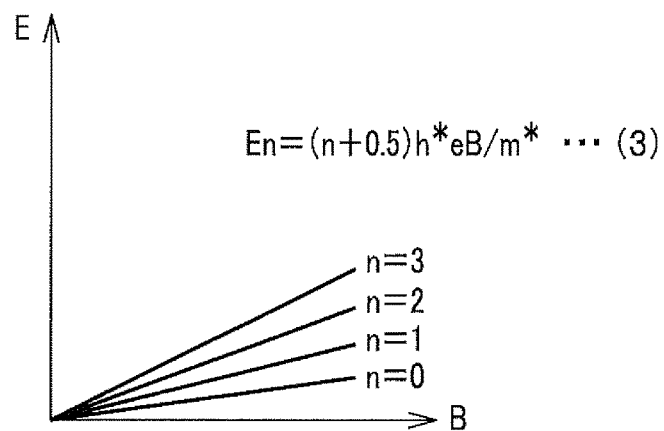
FIG. 11A is a diagram showing the relationship between a magnetic field B and electron energy E in a normal semiconductor.
Figure 11B:
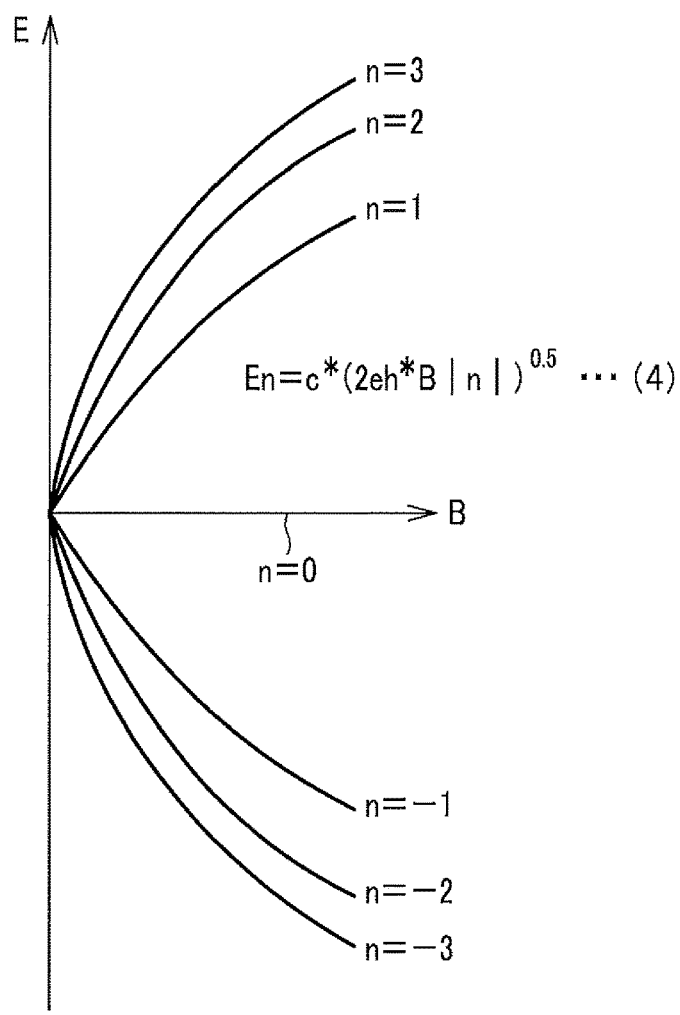
FIG. 11B is a diagram showing the relationship between a magnetic field B and electron energy E in the graphene.

From specific properties of the graphene 32 described above, it is known that energy levels obtained when the magnetic field B is applied as shown in FIG. 5A are represented by the relationships shown in FIG. 11A and FIG. 11B, i.e., the following formulas (3) and (4). FIG. 11A shows the relationship between a magnetic field B and electron energy E in a normal semiconductor. FIG. 11B shows a similar relationship in the graphene 32.

$$\text{Semiconductor: } En=(n+0.5)\hbar*eB/m* \qquad (3)$$

$$\text{Graphene: } En=c*(2eh*B|n|)^{0.5} \qquad (4)$$

In the formulas (3) and (4), c* denotes a velocity of the Dirac-Fermion; e denotes elementary charge; h* denotes 1/(2π) of Planck constant h; B denotes an applied magnetic field; n denotes an exponent of Landau levels; and m* denotes effective mass of electrons in crystal (for example, in the case of GaAs, the effective mass is approximately 0.0665 times larger than the mass of free electrons).

From the above formula (3), the following formula (5) is derived because h*, e, and m* are constants. Herein, C1 is a constant. Similarly, from the above formula (4), the following formula (6) is derived because c*, e, and h* are constants. Herein, C2 is a constant.

$$\text{Semiconductor: } En=C1(n+0.5)B \qquad (5)$$

$$\text{Graphene: } En=C2(Bn|n|)^{0.5} \qquad (6)$$

From the above formula (5), the amount of change ΔE of the electron energy E with respect to the increase of n (n=0, 1, 2, 3) is C1×0.5B and proportional to the applied magnetic field B. The difference between the amounts of change in the cases of n=0, 1, 2, 3 is constant.

In contrast, from the above formula (6), the amount of change ΔE of the electron energy E with respect to the increase of n (n=−3, −2, −1, 0, 1, 2, 3) is proportional to $(B|n|)^{0.5}$, and thus it is understandable that the difference between the amounts of change in the cases of n=−3, −2, −1, 0, 1, 2, 3 is not constant.

The sensor 13A is fabricated focusing on such characteristics of the graphene 32. Description will be given of a method of fabrication of the sensor 13A.

Figure 12A:
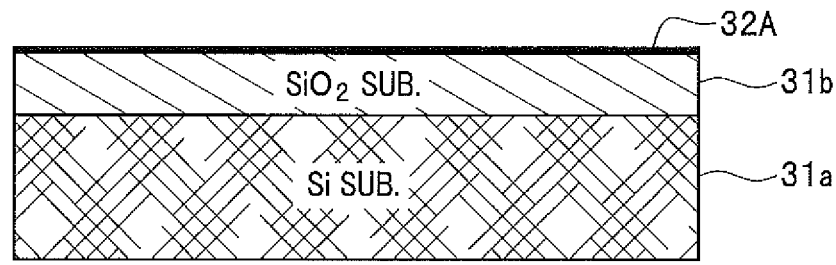
FIG. 12A shows a method of fabrication of the terahertz detection sensor, and is a side view showing a state in which graphene is laminated on an upper surface of a $SiO_2$ substrate laminated on a Si substrate.

As shown in FIG. 12A, a substrate is used in which the graphene 32A is laminated on the upper surface of the SiO$_2$ substrate 31b laminated on the Si substrate 31a.

Figure 12B:
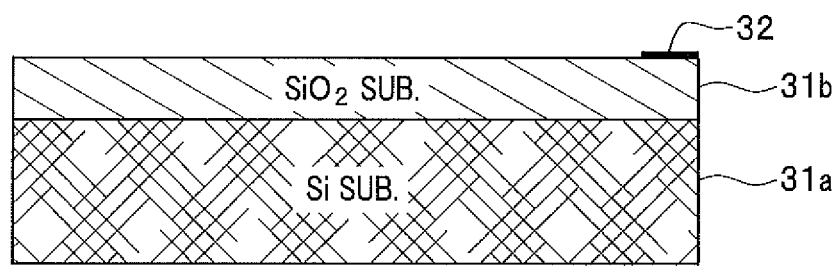
FIG. 12B shows the method of fabrication of the terahertz detection sensor, and is a side view showing a state in which the graphene is cut by etching.

Next, as shown in FIG. 12B, the graphene 32A of a rectangular shape is cut by etching using an oxygen asher or the like and shaped so as to allow one corner of the rectangular parallelepiped to be left as the graphene 32 with a predetermined size and shape. The graphene 32 has a planar shape of a smaller size than a wavelength of terahertz light as in the shape of the two-dimensional electron gas section 22 described above, and is formed into a shape capable of efficiently detecting near-field light of the terahertz light emitted from the sample 18 itself.

Figure 12C:
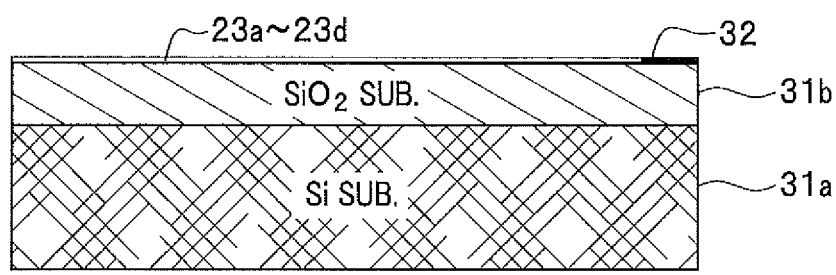
FIG. 12C shows the method of fabrication of the terahertz detection sensor, and is a side view showing a state in which each electrode is formed on the Si substrate.

Next, as shown in FIG. 12C, conductive material such as gold or the like is vapor-deposited on the SiO$_2$ substrate 31b to form each electrode 23a~23d (see FIG. 9), thereby fabricating the sensor 13A. Subsequently, each electrode 23a~23d is connected via the conductive wire 24 to the measurement control unit 20A (FIG. 9).

Next, description will be given of the case where the magnetic field generating unit 19 shown in FIG. 5A applies a magnetic field B to the sensor 13A provided with the graphene 32.

The magnetic field generating unit 19 is configured to include the coil 19a wound so as to surround the optical axis of terahertz light that is emitted from the sample 18 to be irradiated on the sensor 13A, the ammeter 19b adapted to detect an electric current (coil current) that flows through the coil 19a, and the voltmeter 19c adapted to detect a voltage across both ends of the coil 19a. The magnetic field generating unit 19 allows an electric current to flow through the coil 19a, thereby generating the magnetic field B to apply it to the sensor 13A provided with the graphene 32. The magnetic field B can be uniquely determined from the coil current.

When terahertz light emitted from the sample 18 is irradiated on the graphene 32, a phenomenon called photoconduction is observed. The "photoconduction" is a phenomenon by which an electric conductivity changes upon irradiation of light on an insulator or a semiconductor. This phenomenon is caused due to that, in a normal semiconductor, electrons are excited by light absorption from the valence band to the conduction band, or from impurity levels to the conduction band, thereby allowing excessive conduction electrons or positive holes to be generated. Herein, conduction of excessive electrons or positive holes excited to the upper and lower Landau levels with the Fermi level between them brings about a change in electric conductivity. Since the graphene 32 is placed in the magnetic field, an increase in electric conductivity leads to an increase in electric resistivity.

From FIG. 11B and the above formula (6), when photon energy hf of an electromagnetic wave to be irradiated is equal to energy spacing in Landau levels (for example, in the case of n=1 to 2, $C2(B|2|)^{0.5}-C2(B|1|)^{0.5}$), very large absorption of the electromagnetic wave is caused. This phenomenon is called cyclotron absorption (or cyclotron resonance).

The photon energy hf of terahertz light obtained when cyclotron absorption is caused becomes equal to the energy spacing in Landau levels obtained when cyclotron absorption is caused. For example, in the case of n=1 to 2, the following formula (7) is established.

$$hf=C2(B|2|)^{0.5}-C2(B|1|)^{0.5} \qquad (7)$$

Based on the formula (7), the frequency f of terahertz light can be determined from the magnetic field B obtained when cyclotron absorption is caused, because C2 (i.e., h*, e, and m*) other than the magnetic field B are known constants.

That is, as shown in FIG. 5A, the measurement control unit 20A changes the strength (magnetic field value) of the magnetic field B applied to the sensor 13A while changing the value of an electric current which flows through the coil 19a of the magnetic field generating unit 19, and allows the magnetic field value to be set to a magnetic field value for which the terahertz detection signal level (signal level) of the sample 18 detected by the sensor 13A increases prominently. The frequency of the terahertz detection signal with the prominently increased level defines a characteristic resonance frequency (specific frequency). Therefore, the magnetic field value can be allowed to conform to the specific frequency by allowing the magnetic field value to be set to the position at which the signal level increases prominently. In other words, the terahertz frequency can be selected.

The case where the magnetic field value is changed to select the frequency of the terahertz detection signal in this manner will be described with reference to FIGS. 13A to 13D and FIGS. 14A to 14C. Note that, in FIGS. 13A to 13D and FIGS. 14A to 14C, the vertical axis indicates the terahertz detection signal level with an arbitrary scale, and the horizontal axis indicates the magnetic field B with a unit of tesla.

Figure 13A:
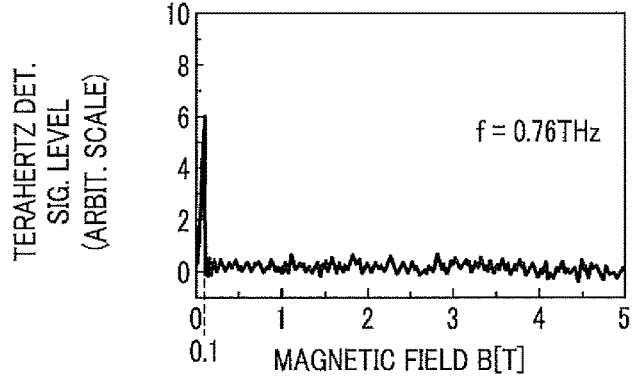
FIG. 13A is a diagram showing a waveform of terahertz light with the specific frequency f=0.76 THz in the case where a terahertz detection signal level in the vertical axis steeply increases for a predetermined magnetic field value in the horizontal axis.

For example, the magnetic field B to be generated by the magnetic field generating unit 19 under control of the measurement control unit 20A is set as shown in FIG. 13A. The example of FIG. 13A allows the specific frequency f=0.76 THz to be selected for a magnetic field value of 0.1 [T] for which the signal level steeply increases to 6, thereby making it possible to display a terahertz image of molecules of the sample 18 that emits a terahertz light with the specific frequency f=0.76 THz.

Figure 13B:
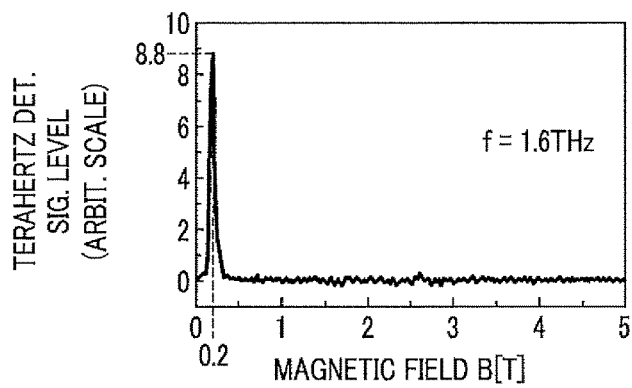
FIG. 13B is a diagram showing a waveform of terahertz light with the specific frequency f=1.6 THz in the case where a terahertz detection signal level in the vertical axis steeply increases for a predetermined magnetic field value in the horizontal axis.
Figure 13C:
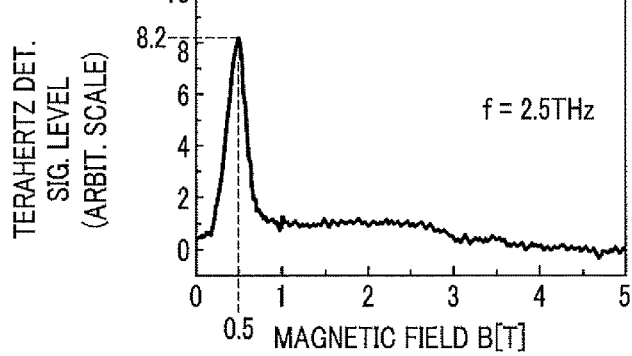
FIG. 13C is a diagram showing a waveform of terahertz light with the specific frequency f=2.5 THz in the case where a terahertz detection signal level in the vertical axis steeply increases for a predetermined magnetic field value in the horizontal axis.
Figure 13D:
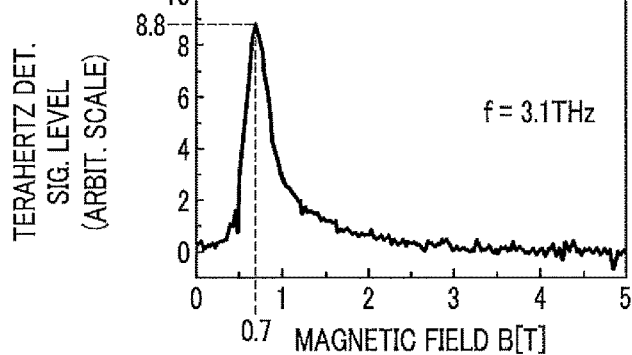
FIG. 13D is a diagram showing a waveform of terahertz light with the specific frequency f=3.1 THz in the case where a terahertz detection signal level in the vertical axis steeply increases for a predetermined magnetic field value in the horizontal axis.

In a similar way, the example of FIG. 13B allows the specific frequency f=1.6 THz to be selected for a magnetic field value of 0.2 [T] for which the signal level steeply increases to 8.8; the example of FIG. 13C allows the specific frequency f=2.5 THz to be selected for a magnetic field value of 0.5 [T] for which the signal level steeply increases to 8.2; and the example of FIG. 13D allows the specific frequency f=3.1 THz to be selected for a magnetic field value of 0.7 [T] for which the signal level steeply increases to 8.8, thereby making it possible to display terahertz images of molecules of the sample that emits terahertz lights with the above selected frequencies, respectively.

Figure 14A:
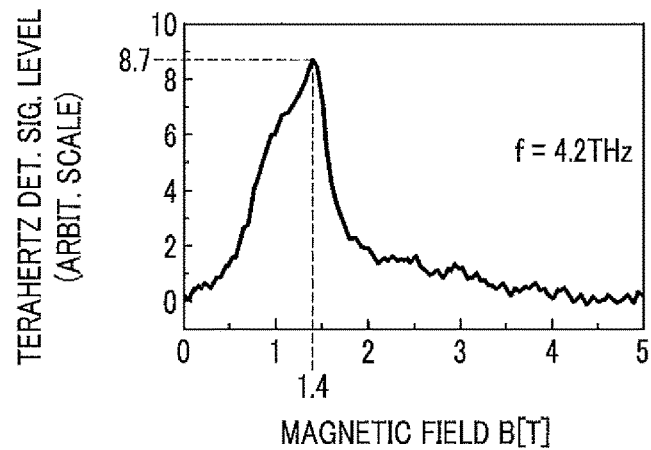
FIG. 14A is a diagram showing a waveform of terahertz light with the specific frequency f=4.2 THz in the case where a terahertz detection signal level in the vertical axis steeply increases for a predetermined magnetic field value in the horizontal axis.
Figure 14B:
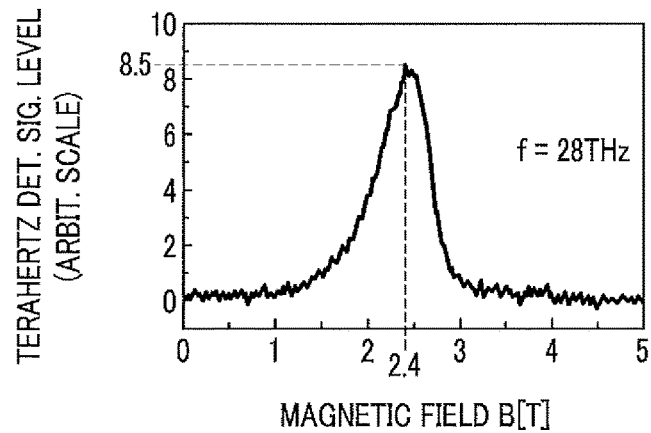
FIG. 14B is a diagram showing a waveform of terahertz light with the specific frequency f=28 THz in the case where a terahertz detection signal level in the vertical axis steeply increases for a predetermined magnetic field value in the horizontal axis.
Figure 14C:
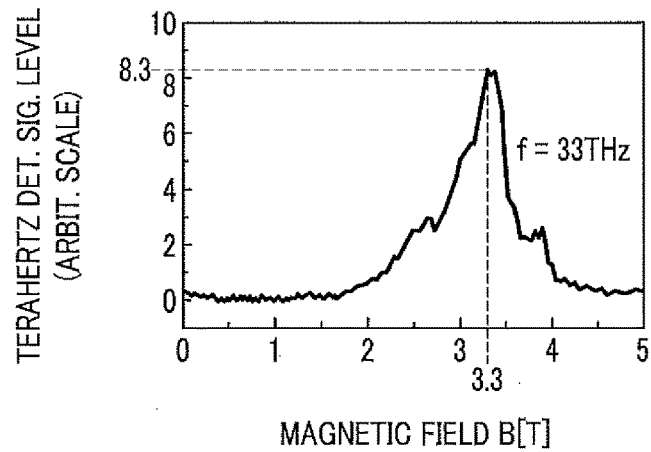
FIG. 14C is a diagram showing a waveform of terahertz light with the specific frequency f=33 THz in the case where a terahertz detection signal level in the vertical axis steeply increases for a predetermined magnetic field value in the horizontal axis.

Moreover, the example of FIG. 14A allows the specific frequency f=4.2 THz to be selected for a magnetic field value of 1.4 [T] for which the signal level steeply increases to 8.7; the example of FIG. 14B allows the specific frequency f=28 THz to be selected for a magnetic field value of 2.4 [T] for which the signal level steeply increases to 8.5; and the example of FIG. 14C allows the specific frequency f=33 THz to be selected for a magnetic field value of 3.3 [T] for which the signal level steeply increases to 8.3, thereby making it possible to display terahertz images of molecules of the sample that emits terahertz lights with the above selected frequencies, respectively.

Note that, with respect to the semiconductor substrate having the graphene 32 shown in FIG. 9 formed on the surface thereof, the example using the Si substrate 31a and the $SiO_2$ substrate 31b is shown, but the semiconductor substrate may be configured using hexagonal boron nitride (h-BN), silicon carbide (SiC) or the like.

Moreover, as long as the detection point has a planar shape of a smaller size than a wavelength of terahertz light in the same way as in the graphene 32 and is formed into a shape capable of efficiently detecting near-field light of the terahertz light emitted from the sample 18, materials such as a superconductor, a semiconductor nanowire, a carbon nanotube or the like may be used as the detection point.

<First Example of the Terahertz Detection Point>

Figure 15:
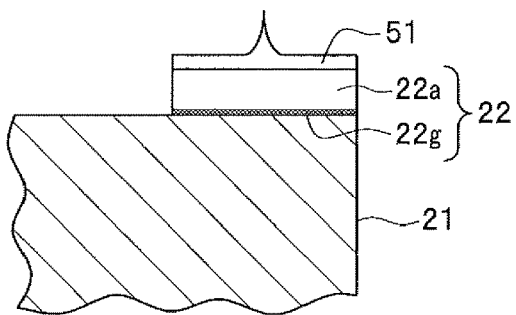
FIG. 15 is a diagram showing a configuration of a terahertz detection point in a first example of the terahertz detection sensor according to the present embodiment.

FIG. 15 is a diagram showing a configuration of a terahertz detection point in a first example of the terahertz detection sensor 13 (FIG. 2) according to the present embodiment.

The detection point in the first example shown in FIG. 15 is formed by integrating a probe 51 having an acicular shape with a sharp point, with the two-dimensional electron gas section 22.

The probe 51 is obtained by forming a metal such as tungsten, or a semiconductor such as silicon, into an acicular shape (or linear shape). Note that silicon is formed into an acicular shape, for example, by anisotropic etching. The probe 51 corresponds to the gate of the MOSFET that controls a region between the source and the drain in the two-dimensional electron gas section 22, and is adapted to control an electron current that flows from the source to the drain on the two-dimensional electron gas 22g, at high speed using the high electron-mobility, with a gate voltage obtained by detecting the near-field light of the terahertz light emitted from the sample 18.

The probe 51 allows a spatial detection size for terahertz light to be reduced because it has an acicular shape with a sharp point, thus making it possible to enhance spatial resolution at the time of detection of the near-field light.

<Second Example of the Terahertz Detection Point>

Figure 16:
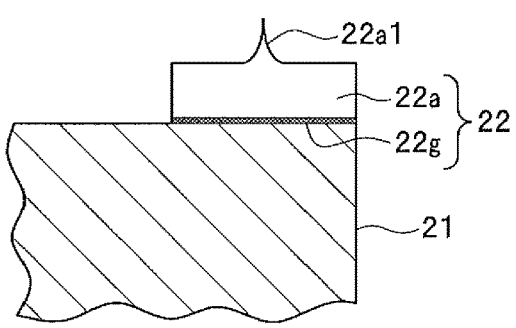
FIG. 16 is a diagram showing a configuration of a terahertz detection point in a second example of the terahertz detection sensor according to the present embodiment.

FIG. 16 is a diagram showing a configuration of a terahertz detection point in a second example of the terahertz detection sensor 13 (FIG. 2) according to the present embodiment.

The detection point in the second example shown in FIG. 16 is provided with a needle-shaped part 22a1 formed by sharpening a part of the surface of the AlGaAs layer 22a in the two-dimensional electron gas section 22. Even the needle-shaped part 22a1 makes it possible, in the same manner as in the probe 51 described above, to control an electron current that flows in the two-dimensional electron gas 22g, at high speed using the high electron-mobility, by detecting the near-field light of the terahertz light emitted from the sample 18. Moreover, the needle-shaped part 22a1 makes it possible, in the same manner as in the probe 51, to enhance spatial resolution at the time of detection of the near-field light.

<Third Example of the Terahertz Detection Point>

Figure 17:
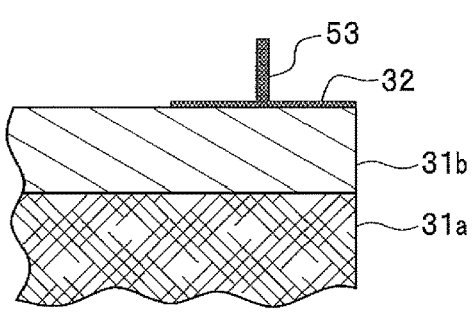
FIG. 17 is a diagram showing a configuration of a terahertz detection point in a third example of the terahertz detection sensor according to the present embodiment.

FIG. 17 is a diagram showing a configuration of a terahertz detection point in a third example of the terahertz detection sensor 13A (FIG. 9) according to the present embodiment.

The detection point in the third example shown in FIG. 17 is provided with a probe 53 formed of an acicular (or linear) carbon nanotube, which is vertically stood on the surface of the graphene 32 that is formed at one corner on the upper surface of the $SiO_2$ substrate 31b on the Si substrate 31a. Even in the case where the probe 53 formed of a carbon nanotube is stood in this way, a spatial detection size for terahertz light is reduced because the probe 53 is formed into an acicular (or linear) shape, thus making it possible to enhance the spatial resolution at the time of detection of the near-field light.

<Fourth Example of the Terahertz Detection Point>

Figure 18:
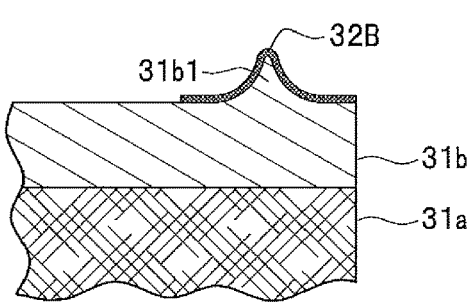
FIG. 18 is a diagram showing a configuration of a terahertz detection point in a fourth example of the terahertz detection sensor according to the present embodiment.

FIG. 18 is a diagram showing a configuration of a terahertz detection point in a fourth example of the terahertz detection sensor 13A (FIG. 9) according to the present embodiment.

The detection point in the fourth example shown in FIG. 18 is provided with a needle-shaped part 31b1 formed by sharpening a part of one corner on the upper surface of the $SiO_2$ substrate 31b, and a graphene 32B formed on the one corner including the needle-shaped part 31b1. According to this configuration, the surface of the graphene 32B is sharpened into an acicular shape in the same manner as in the probe 53 described above, thus making it possible to enhance the spatial resolution at the time of detection of the near-field light.

<Another Example of the Vibration Unit>

Figure 19:
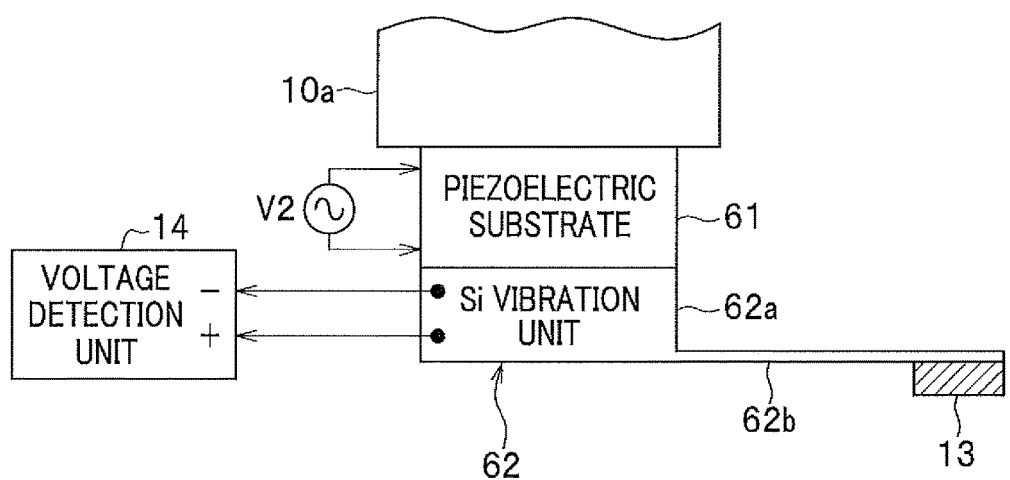
FIG. 19 is a diagram showing a configuration of a Si vibration unit as another example of the vibration unit in the terahertz image measurement device.
Figure 20:
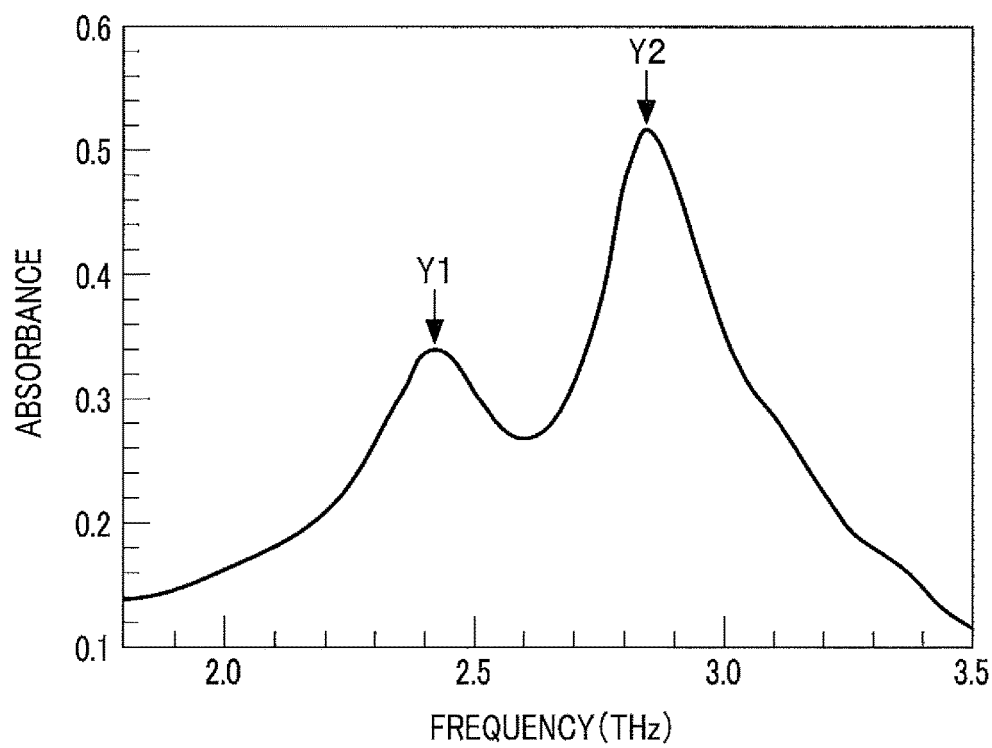
FIG. 20 is a diagram showing a frequency spectrum exhibiting characteristic resonance frequencies in the vicinity of 2.4 THz and in the vicinity of 2.9 THz in PHB (energy storage substance within cells).

FIG. 19 is a diagram showing a configuration of a Si vibration unit 62 as another example of the vibration unit (GaAs vibration unit 11 in FIG. 1) in the terahertz image measurement device 10.

The Si vibration unit 62 is composed of a base end part 62a having a rectangular parallelepiped shape, and a plate-like part 62b flush with a lower surface of the base end part 62a and projecting from the base end part 62a, which are integrally formed in the same manner as in the GaAs vibration unit 11. The sensor 13 is fixed on a lower surface of a tip part of the plate-like part 62b. The base end part 62a is fixed via a piezoelectric substrate 61 to the piezoelectric substrate 10a. Application of a power supply voltage V2 to the piezoelectric substrate 61 causes the Si vibration unit 62 to vibrate with a constant vibration frequency by piezoelectric effect, and in response to this, the plate-like part 62b to vibrate vertically with the same vibration frequency. Moreover, the voltage detection unit 14 is adapted to detect a voltage in response to vibration of the Si vibration unit 62.

Even in the configuration using the Si vibration unit 62 fixed on the piezoelectric substrate 61, the operation of detection of the terahertz light from the sample 18 by the sensor 13 can be maintained at a constant state in the same manner as the cooperative operation of the GaAs vibration unit 11 and the Z-piezoelectric substrate 15 described above. Note that the Si vibration unit 62 constitutes the vibration unit described in the claims. The vibration unit may be composed of a vibration member formed of piezoelectric material or the like, or of a vibration member such as a tuning fork that vibrates in response to vibration of the piezoelectric substrate 61, besides the Si vibration unit 62.

The terahertz image measurement device described above can be put into effect in active measurement, besides the passive measurement.

Other concrete configurations can be appropriately modified within the scope not departing from the gist or essential features of the present invention.

REFERENCE SIGNS LIST

10 Terahertz image measurement device
10a Piezoelectric substrate
11 GaAs vibration unit
12 AC power supply
13, 13A Terahertz detection sensor
14 Voltage detection unit
15 Piezoelectric substrate for Z layer (Z-piezoelectric substrate)
16 Piezoelectric substrate for Y layer (Y-piezoelectric substrate)
17 Piezoelectric substrate for X layer (X-piezoelectric substrate)
18 Sample
19 Magnetic field generating unit
19a Coil
19b Ammeter
19c Voltmeter
20 Measurement control unit
21 GaAs substrate
22 Two-dimensional electron gas section (Detection point)
22a AlGaAs layer
22g Two-dimensional electron gas
23a~23d Electrode
31a Si substrate
31b $SiO_2$ substrate
32 Graphene (Detection point)
51 Probe
53 Probe (Carbon nanotube)
61 Piezoelectric substrate
62 Si vibration unit
B Magnetic field

What is claimed is:

1. A terahertz detection sensor adapted to detect terahertz light, the terahertz detection sensor comprising:
a detection point which has a shape of a smaller size than a wavelength of the terahertz light and in which near-field light of the terahertz light is detected; and
a semiconductor substrate having the detection point formed on a surface thereof; and
a first electrode and a second electrode formed on the surface of the semiconductor substrate, the first electrode being adapted to supply an electric current to the detection point, and the second electrode being adapted to output a voltage detected at a time of detection of the near-field light, to the detection point to which the electric current is supplied through the first electrode.

2. The terahertz detection sensor according to claim 1, wherein:
each of the first electrode and the second electrode is formed into a band-like shape extending with a point thereof tapered like a needle and includes a pair of electrodes joined to the detection point in the needle-like point.

3. The terahertz detection sensor according to claim 1, wherein:
the semiconductor substrate has a high electron mobility transistor structure in which two-dimensional electron gas is distributed in an interface between heterogeneous semiconductor layers laminated up and down and composed of semiconductors of different kinds or structures, and
the detection point has a structure in which an uppermost semiconductor layer of the laminated semiconductor layers is formed into a shape of a smaller size than a wavelength of the terahertz light, and the two-dimensional electron gas is distributed in the interface between the formed semiconductor layer and the semiconductor layer underlying the formed semiconductor layer.

4. The terahertz detection sensor according to claim 3, wherein:
the semiconductor substrate has a high electron mobility transistor structure in which an AlGaAs layer is laminated on a GaAs layer and two-dimensional electron gas is distributed in an interface between the AlGaAs layer and the GaAs layer, and
the detection point has a structure in which the AlGaAs layer is formed into a shape of a smaller size than a wavelength of the terahertz light and the two-dimensional electron gas is distributed in the interface between the formed AlGaAs layer and the GaAs layer.

5. The terahertz detection sensor according to claim 3, wherein:
the detection point is provided with a probe integrated with the detection point, the probe having an acicular or linear shape with a sharp point and formed of either a metal or a semi conductor.

6. The terahertz detection sensor according to claim 1, wherein:
the semiconductor substrate has a structure including semiconductor layers of different kinds laminated up and down, and
the detection point is composed of a graphene formed into a shape of a smaller size than a wavelength of the terahertz light on an uppermost semiconductor layer of the laminated semiconductor layers.

7. The terahertz detection sensor according to claim 6, wherein:
the semiconductor substrate has a structure in which a $SiO_2$ layer is laminated on a Si layer, and
the detection point is composed of a graphene formed into a shape of a smaller size than a wavelength of the terahertz light on the $SiO_2$ layer.

8. The terahertz detection sensor according to claim 6, wherein:
the detection point is provided with a probe integrated with the detection point, the probe having an acicular or linear shape with a sharp point and formed of a carbon nanotube.

9. The terahertz detection sensor according to claim 1, wherein:
each of the first electrode and the second electrode is formed into a band-like shape extending with a point thereof tapered like a needle and includes a pair of electrodes joined to the detection point in the needle-like point, and the electrodes have a length equal to or longer than a wavelength of terahertz wave and are adapted to receive the terahertz wave in a region on which an electric field is concentrated, shorter than the wavelength of the terahertz wave.

10. A terahertz image measurement device comprising:

the terahertz detection sensor according to claim 1, adapted to detect near-field light of terahertz light emitted from a sample;

a magnetic field generating unit that has a coil disposed around the sample and the terahertz detection sensor, the coil being wound so as to surround an optical axis of the terahertz light irradiated on the terahertz detection sensor from the sample, and applies to the terahertz detection sensor a magnetic field generated by allowing an electric current to flow through the coil; and a measurement control unit that allows an electric current to flow through the coil, changes a value of the flowing electric current to set a strength of the magnetic field to a magnetic field value for which a detection signal level of the terahertz light of the sample detected by the terahertz detection sensor increases prominently, and allows the magnetic field value to conform to a specific frequency of the terahertz light.

11. The terahertz image measurement device according to claim 10, further comprising:

a vibration unit that causes the terahertz detection sensor fixed on a plate-like tip part extending from a base end part of the vibration unit, to vibrate in a direction of space between the terahertz detection sensor and the sample, by application of a voltage to the base end part; and a piezoelectric substrate that mounts and fixes the sample thereon via the space between the terahertz detection sensor and the sample, and moves the sample mounted and fixed thereon in the direction of space so as to keep the space constant, in response to a voltage obtained by detecting vibration of the vibration unit.

* * * * *